(12) United States Patent
Smith et al.

(10) Patent No.: US 7,144,707 B2
(45) Date of Patent: Dec. 5, 2006

(54) DETERMINATION OF RISK AND TREATMENT OF COMPLICATIONS OF PREMATURITY

(75) Inventors: Lois Smith, West Newton, MA (US); Ann Hellström, Hovås (SE)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/446,648

(22) Filed: May 28, 2003

(65) Prior Publication Data
US 2004/0053838 A1  Mar. 18, 2004

Related U.S. Application Data

(63) Continuation of application No. PCT/US01/47285, filed on Nov. 13, 2001.

(60) Provisional application No. 60/274,252, filed on Mar. 9, 2001.

(30) Foreign Application Priority Data
Nov. 28, 2000 (SE) .................................. 0004405

(51) Int. Cl.
C12Q 1/68 (2006.01)

(52) U.S. Cl. ........................ 435/7.1; 530/303; 530/350

(58) Field of Classification Search ................ 435/7.1, 435/7.92, 7.94; 530/303, 388.24, 388
See application file for complete search history.

(56) References Cited

U.S. PATENT DOCUMENTS 6,034,059 A   3/2000   Fryklund et al.

FOREIGN PATENT DOCUMENTS

WO   WO 03/012043 A2   2/2003

OTHER PUBLICATIONS

Lineham et al., "Circulating insulin-like growth factor I levels in newborn premature and full-term infants followed longitudinally," early Human development, 1986, 13:37-46.*
Verhaeghe et al., "C-peptide, insulin-like growth factors I and II, and insulin-like grwoth factor binding protein-1 in umbilical cord serum: Correlations with birth weight," Am J Obstet Gynecol, 1993, 169:89-97.*
Hellstrom et al., "Postnatal serum insulin-like growth factor I deficiency is associated with retinopathy of prematurity and other complications of premature birth", Pediatrics, 2003, 112:1016-1020.*
Lofqvist et al., "Postnatal head growth deficit among premature infants parallels retionopathy and insulink-like growth factor-1 deficit" Pediatrics, 2006, 117:1930-1938.*
Msall et al. "Severity of Neonatal Retinopathy of Prematurity is Predictive of Neurodevelopment Functional Outcome at Age 5.5 Years" Pediatrics, 2000, 106:998-1005.*
Smith LE, "IGF-1 and retinopathy of prematurity in the preterm infant" Biol. Neonate, 2005 88:237-244.*
Aiello, L.P. et al.; Proc Natl. Acad. Sci. U S A; 92:10457-61 (1995).
Alon, T. et al.; Nature Medicine; 1(10):1024-8 (1995).
Ashton, N.; Am J. Ophthalmol.; 62(3);:412-35 (1966).
Baker, J. et al.; Cell; 75:73-82 (1993).
Baxter, R.C. et al.; Biochem. Biophys. Res. Comm.; 139(3):1256-1261 (1986).
Blum, W.F. et al.; Modern Concepts In Insulin-Like Growth Factors (E. M. Spencer, ed., Elsevier, New York); pp. 381-393 (1991).
Davis, J.M. et al.; Neonatology: Pathophysiology and Management of the Newborn; pp. 453-477 (1994).
de Lacerda, L. et al.; Clin. Endocrinol.; 51:541-550 (1999).
Flynn, J.T. et al.; Arch. Ophthalmol.; 95:217-223 (1977).
Frank L., Clin. Perinatol.; 19:541-562 (1992).
Gluckman, P.D. et al.; Hormone Research; 48:11-16 (1997).
Hack, M. et al.; The Future of Children; 5:176-196 (1995).
Kinsey, V.E. et al.; Pediatrics; 60(5):655-668 (1977).
Lucey, J.F. et al.; Pediatrics; 73(1):82-96 (1984).
Northway, W.H.; Pediatrics; 89(5):969-973 (1992).
Ozaki, H. et al.; American Journal of Pathology; 156(2):697-707 (2000).
Penn, J.S. et al.; Invest. Ophthalmol. Vis. Sci.; 35(9):3429-3435 (1994).
Pierce, E. A. et al.; Arch Ophthalmol;. 114:1219-1228 (1996).
Rinderknecht, E. et al.; Proc. Natl. Acad. Sci. USA; 73(7):2365-2369 (1976).
Robinson, G.S. et al.; Proc. Natl. Acad. Sci. USA; 93:4851-4856 (1996).
Rush, M.G. et al.; Clinics in Perinatology; 19(3):563-590 (1992).
Simons, B.D. et al.; International Ophthalmology Clinics; 39:29-48 (1999).
Sommer, A. et al.; Modern Concepts Of Insulin-Like Growth Factors (E. M. Spencer, ed., Elsevier, New York); pp. 715-728 (1991).
Southall, D.P. et al.; Archives of Disease in Childhood; 65:1089-1095 (1990).
Stone, J. et al.; The Journal of Neuroscience; 15(7):4738-4747 (1995).
Woods, K.A. et al.; New England Journal of Medicine; 335(18):1363-1367 (1996).

* cited by examiner

*Primary Examiner*—Christina Chan
*Assistant Examiner*—Michael Szperka
(74) *Attorney, Agent, or Firm*—Nixon Peabody LLP

(57) ABSTRACT

In one aspect of the present invention there is provided a method for determining the risk of developing a complication of preterm birth in a patient born before 40 weeks of gestation or weighing 10% less than the average for the patient's gestational age. The method involves measuring serum IGF-I and/or IGF-I binding protein levels after birth of the patient to obtain an IGF-I or IGF-I binding protein level; and correlating said IGF-I or IGF-I binding protein level with an in utero baseline level of IGF-I or IGF-I binding protein based on gestational age matched mean levels in utero, wherein an IGF-I or IGF-I binding protein level below the mean gestational age in utero level indicates the patient is at an increased risk of developing a complication of preterm birth. The complications of preterm birth include retinopathy of prematurity, developmental delay, mental retardation, bronchopulmonary dysplasia, and intraventricular hemorrhage. Methods for treating/preventing complications of preterm birth are also provided.

2 Claims, 9 Drawing Sheets

DETERMINATION OF RISK AND TREATMENT OF COMPLICATIONS OF PREMATURITY

CROSS-REFERENCE TO RELATED APPLICATIONS

This application is a continuation of copending International Application PCT/US01/47285 filed on Nov. 13, 2001, which designated the U.S. and which application is specifically incorporated herein by reference. The non-provisional application, PCT/US01/47285 claims the benefit of priority as applicable under 35 U.S.C. Sections 119(e); 120, 121 and 365(c); and U.S.C. Section 119 to Provisional Application No. 60/274,252, filed on 9 Mar. 2001, and Swedish Patent Application No. 0004405-7, filed on 28 Nov. 2000.

FIELD OF THE INVENTION

The present invention relates generally to determining the risk of developing complications of premature birth and low birth weight, and particularly to complications associated with IGF-I. The present invention further relates to methods for treating such conditions.

BACKGROUND OF THE INVENTION

Of an estimated 4.2 million live births in the United States each year, approximately 383,000 (about 9%) occur prematurely. Preterm labor and its complications are major perinatal public health issues in developed societies today. Low birth-weight infants or infants born prematurely miss a major part of the critical period of in utero growth. They account for half of all infant deaths and three-quarters of long-term morbidity. They impose a heavy burden on the national economy, because of the high costs of special care in both the neonatal period and over the life-span of survivors. Many survivors also have diminished quality of life because of physical damage resulting directly from prematurity.

The length of a normal pregnancy or gestation is considered to be 40 weeks (280 days) from the date of conception. Infants born before 37 weeks gestation are considered premature and may be at risk for complications. Advances in medical technology have made it possible for infants born as young as 23 weeks gestational age (17 weeks premature) to survive. Infants born prematurely are at higher risk for death or serious complications due to their low birth weight and the immaturity of their body systems. Low birthweight, defined by a cut-off of 2,500 g, serves as a marker for high risk newborns, as it is correlated with prenatal risk factors, intrapartum complications and neonatal disease, and is composed largely of preterm births. Studies on very low birth-weight, defined as less than 1,500 g or less than 1,000 g cut-offs that identify infants at highest risk, those with high rates of severe respiratory and neurological complications associated with extreme prematurity. (See, Hack, M., Klein, N. K., & Taylor, H. G., Long-term developmental outcomes of low birth weight infants. The Future of Children, 5,176–196 (1995)).

The lungs, digestive system, and nervous system (including the brain) are not fully developed in premature babies, and are particularly vulnerable to complications. The most prevalent medical problems encountered in preterm infants are retinopathy of prematurity, developmental delay, mental retardation, bronchopulmonary dysplasia, necrotizing enterocolitis, and intraventricular hemorrhage.

Retinopathy of prematurity (ROP) is a potentially blinding disease, initiated by lack of retinal vascular growth after premature birth. The greatest risk factor for development of ROP is low birth weight and gestational age. ROP occurs in two phases. (Simons, B. D. & Flynn, J. T. (1999) *International Ophthalmology Clinics* 39, 29–48). When infants are born prematurely the retina is incompletely vascularized. In infants who develop ROP, growth of vessels slows or ceases at birth leaving maturing but avascular and therefore hypoxic peripheral retina. (Ashton, N. (1966) *Am J Ophthalmol* 62, 412–35; Flynn, J. T., O'Grady, G. E., Herrera, J., Kushner, B. J., Cantolino, S. & Milam, W. (1977) *Arch Ophihalmol* 95, 217–23). This is the first phase of ROP.

The extent of non-perfusion of the retina in the initial phase of ROP appears to determine the subsequent degree of neovascularization, the late destructive stage of ROP, with the attendant risk of retinal detachment and blindness. (Penn, J. S., Tolman, B. L. & Henry, M. M. (1994) *Invest Ophthalmol Vis Sci* 35, 3429–35). If it were possible to allow blood vessels to grow normally in all premature infants, as they do in utero, the second damaging neovascular phase of ROP would not occur. When ROP was first described in 1942, the etiology was unknown. However, the liberal use of high supplemental oxygen in premature infants was soon associated with the disease and hyperoxia was shown to induce ROP-like retinopathy in neonatal animals with incompletely vascularized retinas. This suggested that an oxygen-regulated factor was involved. Expression of vascular endothelial growth factor (VEGF), which is necessary for normal vascular development, is oxygen-regulated and was found to be important for both phases of ROP. (Aiello, L. P., Pierce, E. A., Foley, E. D., Takagi, H., Chen, H., Riddle, L., Ferrara, N., King, G. L. & Smith, L. E. (1995) *Proc Natl Acad Sci USA* 92, 10457–61; Robinson, G. S., Pierce, E. A., Rook, S. L., Foley, E., Webb, R. & Smith, L. E. (1996) *Proc Natl Acad Sci USA* 93, 4851–6; Pierce, E. A., Foley, E. D. & Smith, L. E. (1996) *Arch Ophthalmol* 114, 1219–28; Stone, J., Itin, A., Alon, T., Pe'er, J., Gnessin, H., Chan-Ling, T. & Keshet, E. (1995) *J Neurosci* 15, 4738–47; Alon, T., Hemo, I., Itin, A., Pe'er, J., Stone, J. & Keshet, E. (1995) *Nature Medicine* 1, 1024–8; Ozaki, H., Seo, M. S., Ozaki, K., Yamada, H., Yamada, E., Okamoto, N., Hofmann, F., Wood, J. M. & Campochiaro, P. A. (2000) *American Journal of Pathology* 156, 697–707). High supplemental oxygen affects the first phase of vascular growth in ROP animal models through suppression of VEGF expression. However, with current careful use of moderate oxygen supplementation, the oxygen level in patients is not a significant risk factor for ROP, yet the disease persists, suggesting that other factors are also involved. (Kinsey, V. E., Arnold, H. J., Kalina, R. E., Stem, L., Stahlman, M., Odell, G., Driscoll, J. M., Jr., Elliott, J. H., Payne, J. & Patz, A. (1977) *Pediatrics* 60, 655–68; Lucey, J. F. & Dangman, B. (1984) *Pediatrics* 73, 82–96).

A premature infant has an incompletely developed brain. Because the breathing center in the brain may be immature, many premature infants are vulnerable to neurologic injury caused by bleeding or low oxygen supply in the brain. The neurologic injury (e.g., intraventricular or periventricular hemorrhage, hypoxic injury around the time of birth) and various early infections of premature birth pose risks of developmental delay, i.e., slowed progression in achieving developmental milestones. Children with early developmental delay are considered "at risk" for mental retardation. Mental retardation refers to an impairment in general intellectual functioning, together with global deficits in other life skills, which must develop before age 18. Children born extremely premature are much more likely to develop mental retardation than children born healthy at term. Neurologic injury can be detected by, for example, an electroencephalogram (EEG). EEG provides useful information that reflects the function of the neonatal brain. The EEG may assist in determining brain maturation, focal or generalized abnormalities. EEG tests brain activity in the outer layer of the brain by measuring electrical current from brain nerve cells. Electrodes are attached to various parts of the head and a graph is made of electrical activity. Brain waves can be interpreted according to their frequency (the number of waves per second) and according to their morphology (shape of single waves or of wave groups).

Intraventricular hemorrhage (IVH) is currently the best known cause of central nervous system morbidity in preterm neonates. Virtually all major IVH occurs at gestational age of 28–30 weeks or less. 90% of significant IVH occurs within the first days to week of life in approximately 15–40% of high risk neonates. IVH is a condition in which immature and fragile blood vessels within the brain burst and bleed into the hollow chambers (ventricles) normally reserved for cerebrospinal fluid and into the tissue surrounding them. The severity of IVH is graded according to a scale of I–IV, with I being bleeding confined to a small area around the burst vessels and IV being an extensive collection of blood not only in the ventricles, but in the brain tissue itself. Grades I and II are not uncommon, and the baby's body usually reabsorbs the blood with no ill effects. However, more severe IVH can result in hydrocephalus, a potentially fatal condition in which too much fluid collects in the ventricles, exerting increased pressure on the brain and causing the baby's head to expand abnormally. To drain fluid and relieve pressure on the brain, doctors will either perform lumbar punctures, a procedure in which a needle is inserted into the spinal canal to drain fluids; install a reservoir, a tube that drains fluid from a ventricle and into an artificial chamber under or on top of the scalp; or install a ventricular shunt, a tube that drains fluid from the ventricles into the abdomen, where it is reabsorbed by the body. Infants who are at high risk for IVH usually have an ultrasound examination of the brain in the first week after birth, followed by others if bleeding is detected. Presently, IVH cannot be prevented; however, close monitoring ensures that procedures to reduce fluid in the brain are implemented quickly to minimize possible damage.

Approximately 1% of all infants develop respiratory distress syndrome reflecting pulmonary immaturity. Among infants treated for respiratory distress syndrome in neonatal intensive care units (ICUs), approximately 20 to 30% will develop the most common form of chronic infant lung disease, bronchopulmonary dysplasia (BPD). (Northway W H. *Bronchopulmonary dysplasia: twenty-five years later.* Pediatrics 1992; 89:969–973). Approximately 7,000 new cases of BPD are diagnosed every year. (Davis J M, Rosenfeld W N. *Chronic lung disease.* In: Avery G B, Fletcher M A, MacDonald M G, eds. *Neonatology: pathophysiology and management of the newborn.* Philadelphia, Pa.: J B Lippincott, 1994; 453–477). Among infants with BPD, there is a high rate of hospital readmission (up to 60%) and subsequent death (up to 20%), mainly from cardiopulmonary failure. (Southall D P, Samuels M P. *Bronchopulmonary dysplasia: a new look at management.* Arch Dis Child 1990; 65:1089–1095). Although survival has improved, advances in therapy have not significantly decreased the incidence of BPD. (Frank L. *Antioxidants, nutrition and bronchopulmonary dysplasia.* Clin Perinatol 1992; 19:541–562; Rush M G, Hazinski T A. *Current therapy of bronchopulmonary dysplasia.* Clin Perinatol 1992; 19:563–590). Prematurity, barotrauma, and oxygen toxicity contribute to the pathogenesis of BPD, but the exact mechanisms by which the neonatal lung undergoes such severe disruption in structure and function are incompletely understood.

Insulin growth factor I (IGF-I) is a well-known regulator of postnatal growth and metabolism. See, Baker J, Liu J P, Robertson E J, Efstratiadis A. *Role of insulin-like growth factors in embryonic and postnatal growth.* Cell 1993; 75:73–82. It has a molecular weight of approximately 7.5 kilodaltons (Kd). IGF-I has been implicated in the actions of various other growth factors, since treatment of tissues with such growth factors leads to increased production of IGF-I. However, its role in prenatal growth and development has only recently been recognized. See, Gluckman P D, Harding J E. *The physiology and pathophysiology of intrauterine growth retardation.* Hormone Research 1997; 48:11–6. Experimental data obtained in IGF-I$^{-/-}$ mice suggest that IGF-I play an important role in the third trimester of embryonic growth and development of several tissues. See, Baker J, Liu J P, Robertson E J, Efstratiadis A. *Role of insulin-like growth factors in embryonic and postnatal growth.* Cell 1993; 75:73–82. In support of the IGF-I$^{-/-}$ data in mice, two patients with genetic defects of the IGF-I system were shown to display impaired prenatal growth and development of the central nervous system. One girl had single allele deletion of the IGF-I receptor gene and one boy had partial deletion of the IGF-I receptor gene. See, Woods K A, Camacho-Hubner C, Savage M O, Clark A J. *Intrauterine growth retardation and postnatal growth failure associated with deletion of the insulin-like growth factor I gene.* New England Journal of Medicine 1996; 335:1363–7; and de Lacerda L, Carvalho J A, Stannard B, et al., 1999 *In vitro and in vivo responses to short-term recombinant human insulin-like growth factor-1 (IGF-I) in a severely growth-retarded girl with ring chromosome 15 and deletion of a single allele for the type 1 IGF receptor gene.* Clin. Endocrinol. 51(5): 541–50.

IGF-I has insulin-like activities and is mitogenic (stimulate cell division) and/or is trophic (promote recovery/survival) for cells in neural, muscular, reproductive, skeletal and other tissues. Unlike most growth factors, IGF is present in substantial quantity in the circulation, but only a very small fraction of this IGF is free in the circulation or in other body fluids. Most circulating IGF is bound to the IGF-binding protein, and more particularly to the IGFBP-3. IGFI-I may be measured in blood serum to diagnose abnormal growth-related conditions, e.g., pituitary gigantism, acromegaly, dwarfism, various growth hormone deficiencies, and the like. Although IGF-I is produced in many tissues, most circulating IGF-I is believed to be synthesized in the liver.

Almost all IGF circulates in a non-covalently associated ternary complex composed of IGF-I, IGFBP-3, and a larger protein subunit termed the acid labile subunit (ALS). The IGF-I/IGFBP-3/ALS ternary complex is composed of equimolar amounts of each of the three components. ALS has no direct IGF binding activity and appears to bind only to the IGF-I/IGFBP-3 binary complex. The IGF-I/IGFBP-3/ALS ternary complex has a molecular weight of approximately 150 Kd. This ternary complex is thought to function in the circulation "as a reservoir and a buffer for IGF-I preventing rapid changes in the concentration of free IGF" (Blum et al., pp. 381–393, *Modern Concepts In Insulin-Like Growth Factors* (E. M. Spencer, ed., Elsevier, N.Y., 1991).

IGFBP-3 is the most abundant IGF binding protein in the circulation, but at least five other distinct IGF binding proteins (IGFBPs) have been identified in various tissues and body fluids. Although these proteins bind IGFs, they each originate from separate genes and have unique amino acid sequences. Thus, the binding proteins are not merely analogs or derivatives of a common precursor.

IGF-I and IGF-I binding proteins such as IGFBP-3 may be purified from natural sources or produced by recombinant means. For instance, purification of IGF-I from human serum is well known in the art (Rinderknecht et al. (1976) Proc. Natl. Acad. Sci. USA 73:2365–2369). Production of IGF-I by recombinant processes is shown in EP 0 128 733, published in December of 1984. IGFBP-3 may be purified from natural sources using a process such as that shown by Baxter et al. (1986, Biochem. Biophys. Res. Comm. 139: 1256–1261). Alternatively, IGFBP-3 may be synthesized recombinantly as discussed by Sommer et al., pp. 715–728, *Modern Concepts Of Insulin-Like Growth Factors* (E. M. Spencer, ed., Elsevier, N.Y., 1991). Recombinant IGFBP-3 binds IGF-I in a 1:1 molar ratio.

Despite the increasing advances in the understanding of complications of prematurity, there are no presently available effective treatments or methods of determining the risk of developing these life-threatening conditions, as premature morbidity and death is very prevalent.

SUMMARY OF THE INVENTION

In one aspect of the present invention there is provided a method for determining the risk of developing a complication of preterm birth in a patient born before 40 weeks of gestation or weighing 10% less than the average for the patient's gestational age. The method involves measuring serum IGF-I and/or IGF-I binding protein levels after birth of the patient to obtain an IGF-I or IGF-I binding protein level; and correlating said IGF-I or IGF-I binding protein level with an in utero baseline level of IGF-I or IGF-I binding protein based on gestational age matched mean levels in utero, wherein an IGF-I or IGF-I binding protein level below the mean gestational age in utero level indicates the patient is at an increased risk of developing a complication of preterm birth. The complications of preterm birth include retinopathy of prematurity, developmental delay, mental retardation, bronchopulmonary dysplasia, and intraventricular hemorrhage.

In another aspect of the invention, there is provided a method for treating a patient suffering from a complication of preterm birth or preventing a patient from developing a complication of preterm birth. The method involves administering to a patient having a serum level IGF-I below the norm for in utero, an effective amount of IGF-I, an analog, or an agonist thereof to elevate the patient's IGF-I level to an in utero baseline level. The in utero baseline level is preferably elevated to a concentration from 10 µg/L to 150 µg/L. In one embodiment of the invention, IGF-I or an analog thereof is administered in combination with an IGF binding protein capable of binding IGF-I. In the preferred embodiment, the IGF binding protein capable of binding IGF-I is IGF-I biding protein 3 (IGFBP-3). The IGF-I or an analog thereof (with or without the IGF binding protein capable of binding IGF-I), or an agonist thereof is administered subcutaneously, intravenously, intramuscularly, or orally. Oral administration is preferred.

In yet another aspect of the invention there is provided use of an IGF-I, an analog or an agonist thereof in the manufacture of a medicament for treating a complication of preterm birth.

Finally, there is also provided an article of manufacture comprising packaging material and a pharmaceutical agent contained within the packaging material. The packaging material comprises a label which indicates that the pharmaceutical may be administered, for a sufficient term at an effective dose, for treating and/or preventing complications associated with preterm birth. The pharmaceutical agent comprises IGF-I or an analog, or an agonist thereof together with a pharmaceutically acceptable carrier.

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention. In the drawings.

In FIG. 6A, VEGF mRNA is visualized anterior to the growing vessels in flat-mounted retina. FIG. 6B shows the area containing VEGF (insert) removed by laser microdissection in both IGF-$1^{-/-}$ mice and control IGF-1$^{+/+}$ retinal cross sections, and VEGF mRNA analyzed by qRT-PCR relative to cyclophilin control.

FIG. 9A shows that in utero, VEGF is found at the growing front of vessels. IGF-1 is sufficient to allow vessel growth. FIG. 9B shows that with premature birth, IGF-1 is not maintained at in utero levels and vascular growth ceases, despite the presence of VEGF at the growing front of vessels. Both endothelial cell survival (AKT) and proliferation (MAPK) pathways are compromised. With low IGF-1 and cessation of vessel growth, a demarcation line forms at the vascular front. High oxygen exposure (as occurs in animal models and in some premature infants) may also suppress VEGF, further contributing to inhibition of vessel growth. FIG. 9C shows that as the premature infant matures, the developing but non-vascularized retina becomes hypoxic. VEGF increases in retina and vitreous. With maturation, the IGF-1 level slowly increases. FIG. 9D shows that when the IGF-1 level reaches a threshold at ~34 weeks gestation, with high VEGF levels in the vitreous, endothelial cell survival and proliferation driven by VEGF may proceed. Neovascularization ensues at the demarcation line, growing into the vitreous. If VEGF vitreal levels fall, normal retinal vessel growth can proceed. With normal vascular growth and blood flow, oxygen suppresses VEGF expression, so it will no longer be overproduced. If hypoxia (and elevated levels of VEGF) persist, further neovascularization and fibrosis leading to retinal detachment can occur.

DETAILED DESCRIPTION

Figure 1:
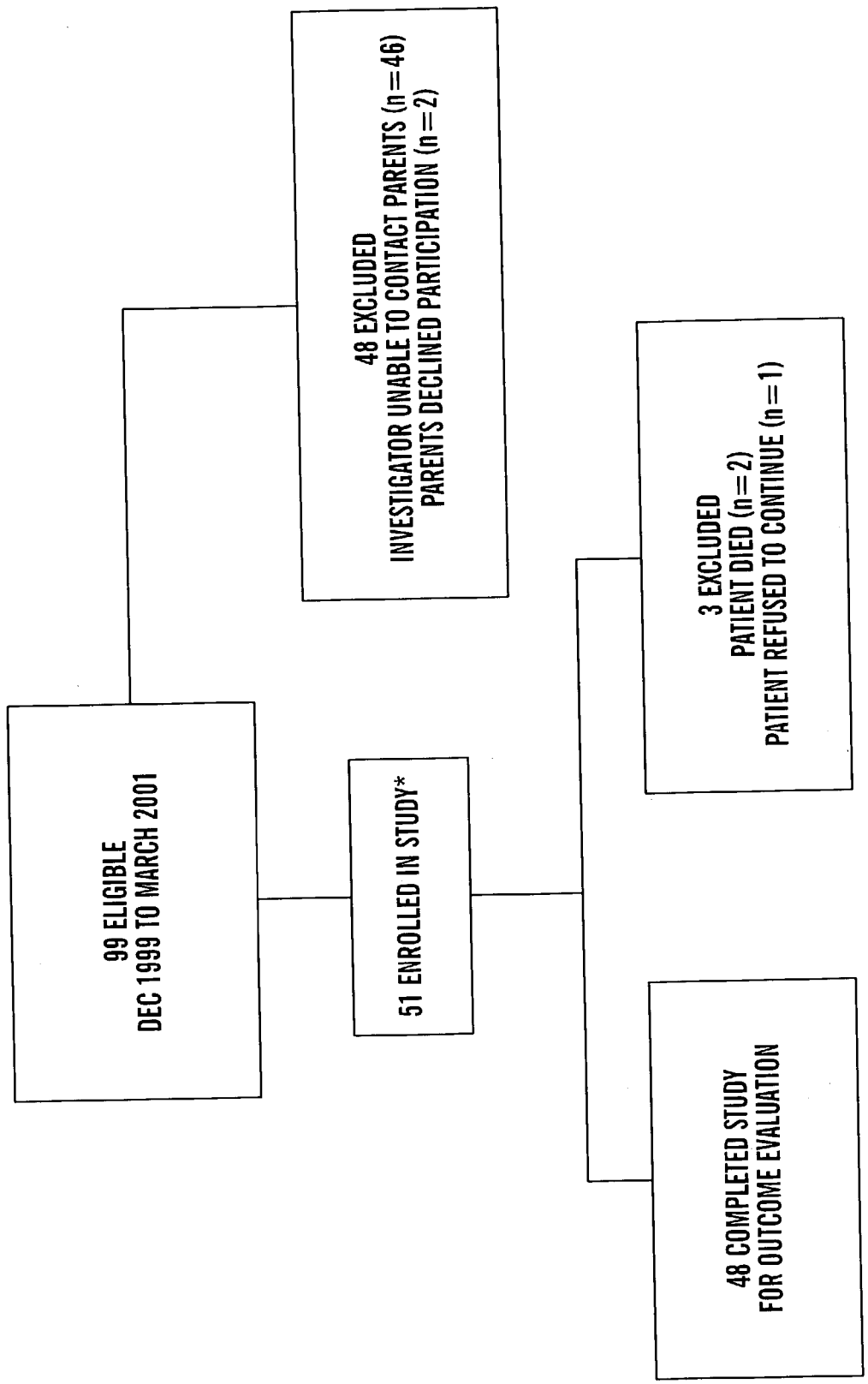
FIG. 1 represents inclusion of study subjects. The scheme illustrates 99 very preterm infants eligible for study of growth factors and postnatal morbidity. All children with a gestational age <27 weeks belonged to this group.

We demonstrated in a mouse model that insulin-like growth factor 1 (IGF-I) is necessary for normal development of retinal blood vessels. See, Hellstrom A, Perruzzi C, Ju M, et al. Low IGF-I suppresses VEGF-survival signaling in retinal endothelial cells: direct correlation with clinical retinopathy of prematurity. Proc Natl Acad Sci USA. 2001; 98:5804–8. See also Example #2 infra. Retinopathy of prematurity (ROP) is associated with abnormal retinal development in which the retinal vessel growth lags behind development in utero. We conducted a prospective longitudinal study measuring serum IGF-I levels weekly in premature infants from birth (post-menstrual age 24 to 32 weeks) until discharge from the hospital. Infants were evaluated for ROP and other morbidity of prematurity: bronchopulmonary dysplasia (BPD), intraventricular hemorrhage (IVH) and necrotizing enterocolitis (NEC). We have found that persistent low serum levels of IGF-I after premature birth are associated with complications of prematurity such as ROP. Therefore, we have devised methods of determining the risk and treating complications associated with preterm birth.

In the third trimester of pregnancy, fetal IGF-I levels rise rapidly in utero and this increase is associated with development of fetal tissue. See, Gluckman P D, Harding J E. The physiology and pathophysiology of intrauterine growth retardation. Hormone Research 1997; 48:11–6. IGF-I levels after premature birth are lower than post-menstrual-age-matched fetal levels in utero, particularly at post-menstrual ages corresponding to the third trimester. See, Lineham J D, Smith R M, Dahlenburg G W, et al. Circulating insulin-like growth factor I levels in newborn premature and full-term infants followed longitudinally. Early Hum Dev 1986; 13:37–46. In IGF-I$^{-/-}$ mice, absence of IGF-I prevents normal retinal vascular growth See, Hellstrom A, Perruzzi C, Ju M, et al. Low IGF-I suppresses VEGF-survival signaling in retinal endothelial cells: direct correlation with clinical retinopathy of prematurity. Proc Natl Acad Sci USA. 2001; 98:5804–8. In premature infants who develop ROP, cessation of normal retinal vascular growth precedes proliferative retinopathy. We hypothesized that in premature babies, ROP and other postnatal morbidity might be a result of abnormal tissue maturation associated with an inability of some prematurely born infants to attain serum IGF-I levels comparable to those normally found in utero.

The relative risk for ROP and other morbidity was increased 5.7-fold (95% confidence interval 2.2–14.6) if IGF-I was $\leq 30$ μg/L at 33 weeks post-menstrual age. After adjustment for post-menstrual age, each increase of 5 μg/L mean IGF-I during post-menstrual age 31–35 weeks decreased the risk of ROP by 59%. The median level of IGF-I at 31–35 weeks of gestation was 26 μg/L (range 17–49) for infants with ROP and other morbidity (n=19), compared to 38 μg/L (range 20–59) in the group without postnatal morbidity (n=29), p<0.0001.

Figure 2A:
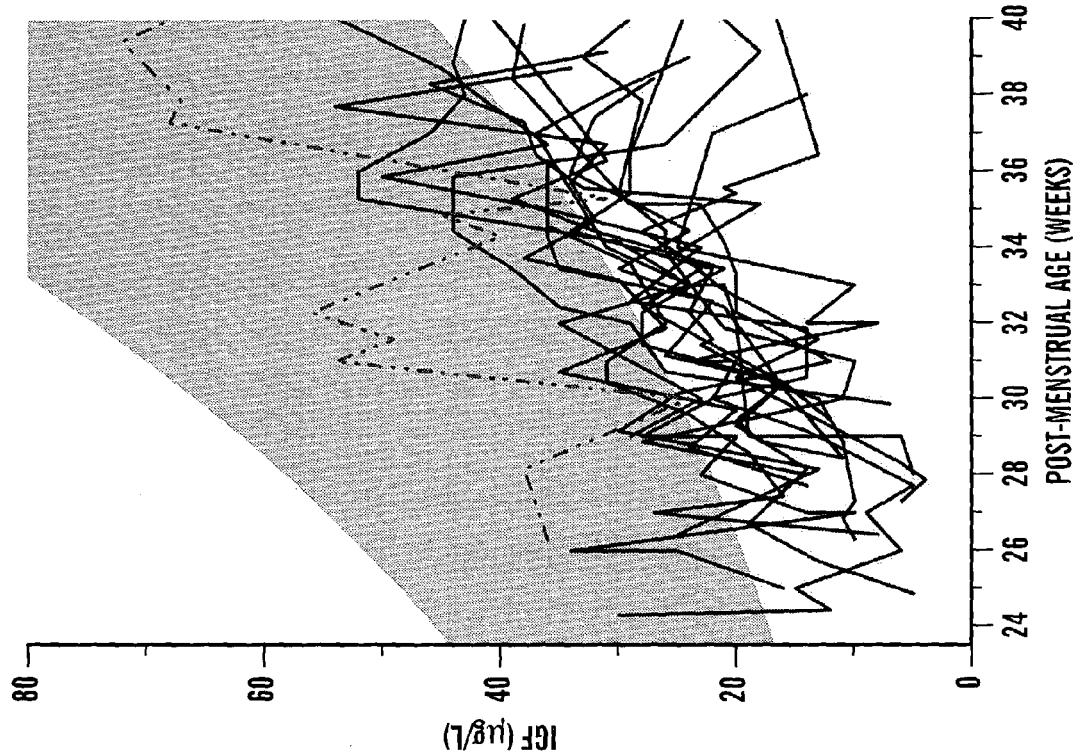
FIGS. 2A and 2B illustrate individual longitudinal pattern of IGB-I levels in premature infants (FIG. 2A) without retinopathy of prematurity (ROP) (n=31) and (FIG. 2B) with ROP (n=17). The gray area depicts the 90% confidence interval for IGF-I values using the technique of cordocentesis and a similar IGB-I assay as used in the present study. Dotted lines indicate individual longitudinal IGB-I values of a twin-pair.
Figure 2B:
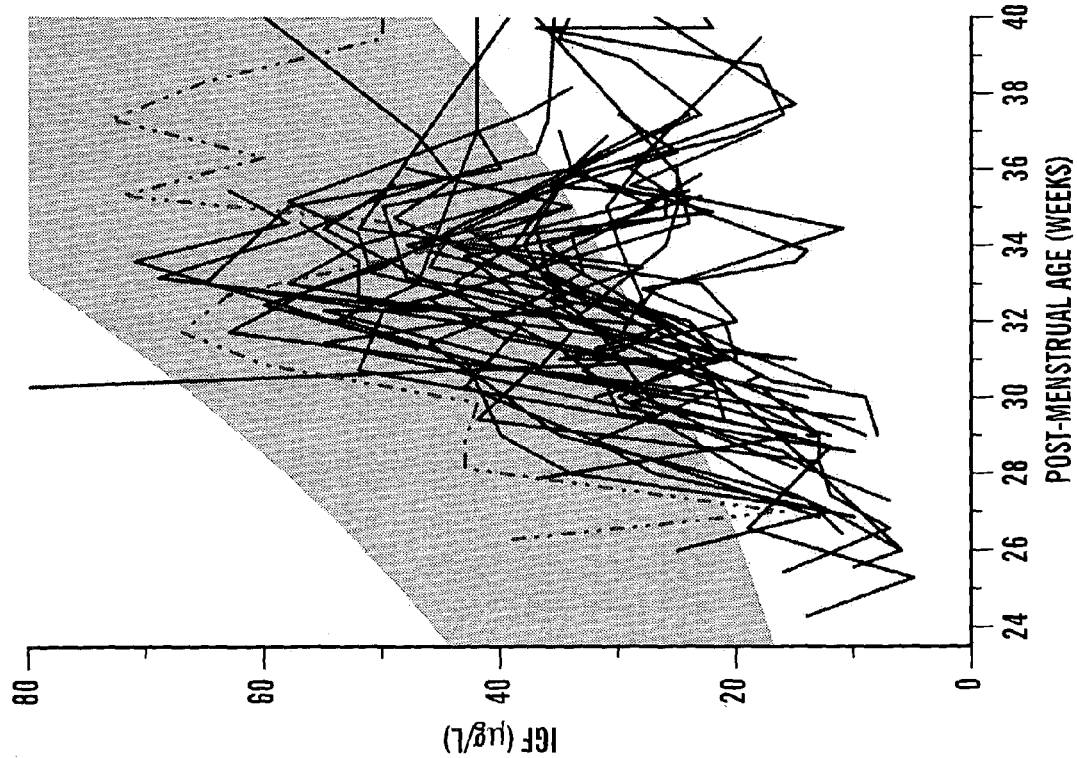

Preterm infants who develop ROP and other postnatal morbidities (BPD, IVH and NEC) have low serum levels of IGF-I after birth compared to infants without ROP and other complications. The serum levels of IGF-I in infants with ROP displayed a slow relatively linear rise during gestational weeks 31–36. In contrast, serum levels of IGF-I in infants without ROP or other postnatal morbidities tended to have a different pattern and increased more rapidly, reaching levels close to those seen in utero, with a maximum IGF-I value at an age corresponding to gestational weeks 31–35 (FIG. 2). Therefore, serum IGF-I levels predict complications of preterm birth, such as ROP. Prematurity per se (gestational or post-menstrual age and birth weight) has historically been by far the strongest risk factor for ROP. See, Simons B D, Flynn J T. Retinopathy of prematurity and associated factors. International Ophthalmology Clinics 1999; 39:29–48. However, we found that the mean IGF-I level at post-menstrual weeks 31–35 was as important as the degree of prematurity per se (post-menstrual age at birth) as a predictive factor for ROP and other complications of prematurity.

The peak level of IGF-I seen in premature infants without morbidity occurred during a critical developmental period in utero when significant maturation of the eyes, lungs, kidneys and brain normally takes place. See, O'Rahilly R, Muller F. Human Embryology and Teratology. New York: Wiley-Liss, 1996. It was recently shown experimentally that IGF-I is important to the action of vascular endothelial growth factor (VEGF) in regulating retinal vascular growth. In retinal vascular endothelial cells, minimum levels of IGF-I are necessary for maximum VEGF activation of the MAPK and Akt pathways, important for endothelial cell survival and proliferation. See, Hellstrom A, Perruzzi C, Ju M, et al. Low IGF-I suppresses VEGF-survival signaling in retinal endothelial cells: direct correlation with clinical retinopathy of prematurity. Proc Natl Acad Sci USA. 2001; 98:5804–8; and Smith L E, Shen W, Perruzzi C, et al. Regulation of vascular endothelial growth factor-dependent retinal neovascularization by insulin-like growth factor-i receptor. Nature Medicine 1999; 5:1390–5. The level of IGF-I required for maximum VEGF activation of the Akt pathway corresponded to the level seen in premature infants who did not develop ROP. The critical role of the IGF-I system in retinal vascular development has been supported in a clinical study where patients with genetic defects in the IGF-I or IGF-I receptor were found to have a reduced number of retinal vascular branching points (Hellström, personal observation). Thus, the reduced serum levels of IGF-I seen in these infants may cause some of the morbidity associated with prematurity.

The major fetal source of IGF-I is the placenta, although ingested amniotic fluid may also provide IGF-I to the fetus. See, Bauer M K, Harding J E, Bassett N S, et al. Fetal growth and placental function. Molecular & Cellular Endocrinology 1998; 140:115–20. Several studies have shown that, in utero, umbilical cord levels of IGF-I are higher than postnatal serum levels in post-menstrual age-matched preterm infants. See, Lineham J D, Smith R M, Dahlenburg G W, et al. Circulating insulin-like growth factor I levels in newborn premature and full-term infants followed longitudinally. Early Hum Dev 1986; 13:37–46. In a preterm baby, the gastrointestinal development is not fully completed at birth and thus enteral nutrition may not be tolerated. As IGF-I is a nutrition-dependent factor, the low serum levels found among some preterm infants might be explained by deficient general nutrition. See, Smith W J, Underwood L E, Keyes L, Clemmons D R. Use of insulin-like growth factor I (IGF-I) and IGF-binding protein measurements to monitor feeding of premature infants. J Clin Endocrinol Metab 1997; 82:3982–8. However, as it has been shown that enteral IGF-I administration enhances gastrointestinal development in fetal sheep, a combination of exogenous IGF-I and adequate general nutrition may be necessary in order to obtain optimal development after premature birth. See, Kimble R M, Breier B H, Gluckman P D, Harding J E. Enteral IGF-I enhances fetal growth and gastrointestinal development in oesophageal ligated fetal sheep. Journal of Endocrinology 1999; 162:227–35.

Definitions

"Preterm" or "preterm birth" or "prematurity" refers to birth of a patient prior to 40 weeks of gestation or weighing 10% less than the average for the patient's gestational age.

"IGF-I" refers to insulin-like growth factor I from any species, including bovine, ovine, porcine, equine, and human, preferably human, and, if referring to exogenous administration, from any source, whether natural, synthetic, or recombinant, provided that it will bind IGF binding protein at the appropriate site. IGF-I can be produced recombinantly, for example, as described in PCT publication WO 95/04076.

An "IGFBP" or an "IGF binding protein" refers to a protein or polypeptide from the insulin-like growth factor binding protein family and normally associated with or bound or complexed to IGF-I whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., Proc. Natl. Acad. Sci. USA, 92: 4472–4476 (1995) and Oh et al., J. Biol. Chem., 271: 30322–30325 (1996). PSF is described in Yamauchi et al., Biochemical Journal, 303: 591–598 (1994). ESM-1 is described in Lassalle et al., J. Biol. Chem., 271: 20458–20464 (1996). For other identified IGFBPs, see, e.g., EP 375,438 published Jun. 27, 1990; EP 369,943 published May 23, 1990; WO 89/09268 published Oct. 5, 1989; Wood et al., Molecular Endocrinology, 2: 1176–1185 (1988); Brinkman et al., The EMBO J., 7: 2417–2423 (1988); Lee et al., Mol. Endocrinol., 2: 404–411 (1988); Brewer et al., BBRC, 152: 1289–1297 (1988); EP 294,021 published Dec. 7, 1988; Baxter et al., BBRC, 147: 408–415 (1987); Leung et al., Nature, 330: 537–543 (1987); Martin et al., J. Biol. Chem., 261: 8754–8760 (1986); Baxter et al., Comp. Biochem. Physiol., 91B: 229–235 (1988); WO 89/08667 published Sep. 21, 1989; WO 89/09792 published Oct. 19, 1989; and Binkert et al., EMBO J., 8: 2497–2502 (1989).

"IGFBP-3" refers to insulin-like growth factor binding protein 3. IGFBP-3 is a member of the insulin-like growth factor binding protein family. IGFBP-3 may be from any species, including bovine, ovine, porcine and human, in native-sequence or variant form, including but not limited to naturally-occurring allelic variants. IGFBP-3 may be from any source, whether natural, synthetic or recombinant, provided that it will bind IGF-I at the appropriate sites. IGFBP-3 can be produced recombinantly, as described in PCT publication WO 95/04076.

A "therapeutic composition," as used herein, is defined as comprising IGF-I, an analog thereof, or IGF-I in combination with its binding protein, IGFBP-3 (IGF-I/IGFBP-3 complex). The therapeutic composition may also contain other substances such as water, minerals, carriers such as proteins, and other excipients known to one skilled in the art.

"Analogs" of IGF-I are compounds having the same therapeutic effect as IGF-I in humans or animals. These can be naturally occurring analogs of IGF-I (e.g., truncated IGF-I) or any of the known synthetic analogs of IGF-I. See, for example, U.S. Pat. No. 5,473,054 for analog compounds of IGF-I.

"Agonists" of IGF-I are compounds, including peptides, which are capable of increasing serum and tissue levels of IGF, especially IGF-1, in a mammal and particularly in a human. See, for example, U.S. Pat. No. 6,251,865 for IGF agonist molecules.

"Developmental delay" as used herein shall mean abnormal neurogenesis which has the potential of leading to slowed mental progression in achieving developmental milestones. Developmental delay can, in some cases, be determined by means of electroencephalogram.

The present invention provides, in one aspect, a method for determining the risk of developing a complication of preterm birth in a patient born before 40 weeks of gestation or weighing 10% less than the average for the patient's gestational age. The method involves measuring serum IGF-I and/or IGF binding protein levels after birth of the patient to obtain an IGF-I level or a level of IGF binding protein capable of binding IGF-I; and correlating said levels of IGF-I or IGF binding protein capable of binding IGF-I with an in utero baseline level of IGF-I or IGF binding protein based on gestational age matched mean levels in utero, wherein an IGF-I level or a level of IGF binding protein capable of binding IGF-I below the mean gestational age in utero level indicates the patient is at an increased risk of developing a complication of preterm birth. The complications of preterm birth suitable for the methods of the present invention include retinopathy of prematurity, developmental delay, mental retardation, bronchopulmonary dysplasia, necrotizing enterocolitis, and intraventricular hemorrhage.

The level of IGF and IGF binding protein capable of binding IGF-I can also be measured via a method which uses antibodies, called the ligand-mediated immunofunctional method (LIFA). This method is disclosed in U.S. Pat. No. 5,593,844, the disclosure of which, regarding antibodies and other materials and conditions that can be used in the assay, is incorporated herein by reference.

Suitable commercially-available IGF antibodies include Nos. 5345-0329 and 5345-0209 of Biogenesis Ltd., Poole, Dorset, UK; GF006 of Chemicon International Inc., Temecula, CA, USA; SC-7144 and SC-1422 of Santa Cruz Biotechnology Inc., Santa Cruz, Calif., USA; and MAS 974p of Harlan Sera-Lab Ltd., Loughborough, Leicestershire, UK.

In another aspect of the invention, there is provided a method for treating a patient suffering from a complication of preterm birth or preventing a patient from developing a complication of preterm birth. The method involves administering to a patient having a serum level IGF-I below the norm for in utero, an effective amount of IGF-I or an analog, or an agonist thereof to elevate the patient's IGF-I level to an in utero baseline level. The in utero baseline level is preferably elevated to a concentration from 10 μg/L to 150 μg/L. In one embodiment of the invention, IGF-I or an analog thereof is administered in combination with IGF binding protein capable of binding IGF-I. In the preferred embodiment, the IGF binding protein capable of binding IGF-I is IGF binding protein 3 (IGFBP-3). The IGF-I or analog or an agonist thereof may be administered subcutaneously, intramuscularly, intravenously or orally. Oral administration is preferred.

It is preferred that the methods of the present invention be initiated soon after birth in order to effectively prevent complications of prematurity and to promote normal vascular development. This is especially critical for the treatment of ROP, wherein increasing IGF-I late in the course of the disease may promote the late neovascular, destructive phase of ROP. See, O'Rahilly R, Muller F. Human Embryology and Teratology. New York: Wiley-Liss, 1996; and Smith L E, Kopchick J J, Chen W, et al. Essential role of growth hormone in ischemia-induced retinal neovascularization. Science 1997; 276:1706–9. The treatment which is delayed until after the non-vascularized retina becomes hypoxic might trigger abnormal retinal neovascularization.

Administration of IGF-I or an analog or an agonist thereof, or IGF-I of an analog thereof in combination with IGF binding protein results in increases in circulating levels of IGF-I. Accordingly, administration of IGF-I or IGF-I in combination with IGF binding protein is useful for the treatment or prevention of symptoms, disorders, and conditions associated with low circulating levels of IGF-I.

The inventive methods disclosed herein provide for the parenteral an oral administration of IGF-I, an analog or an agonist thereof, or IGF-I or an analog in combination with IGF binding protein complex to infants in need of such treatment. Parenteral administration includes, but is not limited to, intravenous (IV), intramuscular (IM), subcutaneous (SC), intraperitoneal (IP), intranasal, and inhalant routes. In the method of the present invention, IGF-I, an agonist or an analog thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the patient. In general, a dose that is administered by subcutaneous injection will be greater than the therapeutically-equivalent dose given intravenously or intramuscularly. Preferably, the dose of IGF-I or an analog thereof administered will be from about 25 μg/kg to about 2 mg/kg of body weight. More preferably, the dose of IGF-I, an agonist, or an analog thereof will be from about 50 μg/kg to about 1 mg/kg.

A composition comprising equimolar amounts of IGF-I and IGF binding protein may be used. Preferably the IGF-I and IGF binding protein are complexed prior to administration. Preferably, the complex is formed by mixing approximately equimolar amounts of IGF-I and IGF binding protein dissolved in physiologically compatible carriers such as normal saline, or phosphate buffered saline solution. More preferably, a concentrated solution of recombinant human IGF-I and a concentrated solution of recombinant human IGF binding protein are mixed together for a sufficient time to form an equimolar complex. Most preferably, recombinant human IGF-I and recombinant human IGF binding protein are combined to form a complex during purification, as described in International Patent Application No. WO 96/40736.

For parenteral or oral administration, compositions of the complex may be semi-solid or liquid preparations, such as liquids, suspensions, and the like. Physiologically compatible carriers are those that are non-toxic to recipients at the dosages and concentrations employed and are compatible with other ingredients of the formulation. For example, the formulation preferably does not include oxidizing agents and other compounds that are known to be deleterious to polypeptides. Hence, physiologically compatible carriers include, but are not limited to, normal saline, serum albumin, 5% dextrose, plasma preparations, and other protein-containing solutions. Optionally, the carrier may also include detergents or surfactants.

In yet another aspect of the invention there is provided use of an IGF-I, an agonist or analog thereof in the manufacture of a therapeutic composition for treating a complication of preterm birth.

Finally, there is also provided an article of manufacture comprising packaging material and a pharmaceutical agent contained within the packaging material. The packaging material comprises a label which indicates that the pharmaceutical may be administered, for a sufficient term at an effective dose, for treating and/or preventing complications associated with preterm birth. The pharmaceutical agent comprises IGF-I, an agonist or an analog thereof together with a pharmaceutically acceptable carrier.

For therapeutic applications, IGF-I or an analog thereof may be suitably administered to a patient, alone or as part of a pharmaceutical composition, comprising the IGF-I or an analog thereof together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, nasal, topical (including buccal and sublingual), or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy. See, for example, *Remington's Pharmaceutical Sciences*, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

The invention will be further characterized by the following examples which are intended to be exemplary of the invention.

EXAMPLE 1

Study Subjects

All eligible patients were at high risk of developing ROP and other morbidity on the basis of their postmenstrual ages at birth. All infants born at a post-menstrual age of less than 32 weeks at The Queen Silvia Children's Hospital in Göteborg between December 1999 and May 2001 were eligible for the study. Exclusion criteria were inability to complete postnatal clinical follow-up until an age corresponding to 40 post-menstrual weeks and any conspicuous congenital anomaly.

Ninety-nine eligible babies were born at The Queen Silvia Children's Hospital, Göteborg between December 1999 and May 2001. Forty-eight infants were excluded because the investigator was unable to contact the parents in time to initiate the study (FIG. 1). The mean post-menstrual age at birth among the excluded children was 30 weeks; no child in this group had a post-menstrual age at birth of less than 27 weeks. Fifty-one infants were identified as potential participants in the study. The parents of these 51 patients all gave permission for participation of their child. After data collection was completed, permission to publish the data was withdrawn by the parents of one baby, who consequently was excluded. In the first 20 days of life two infants died.

In total, 48 babies, including 6 twin pairs, with a median post-menstrual age at birth of 27.0 weeks (range 24.0–31.8 weeks) were included. All children were hospitalized in a neonatal intensive care unit. Gestational age at birth was based on fetal ultrasonography, performed at week 16 post-menstruation. Twenty-seven of the children were included in a previously reported study on cross-sectional IGF-I values and ROP. See, Hellstrom A, Perruzzi C, Ju M, et al. Low IGF-I suppresses VEGF-survival signaling in retinal endothelial cells: direct correlation with clinical retinopathy of prematurity. Proc Natl Acad Sci USA. 2001; 98:5804–8.

Nutrition

All infants were nourished according to the routines for premature babies at the neonatal unit. Oral feeding with increasing amounts of human/maternal breast-milk was introduced during the first or second day of life. At three days of age, parenteral nutrition was introduced if the child could not tolerate oral feeding with at least half the amount of the scheduled 24-hours requirement. The breast-milk given to children with a birth-weight below 1500 grams was fortified with 0.8 g protein per 100 ml breast-milk (gradually introduced over one week) from 10 days of age until the baby weighed 2000 grams.

IGF-I Analysis

Without knowledge of ROP status, intravenous blood-samples (0.5 ml) were taken weekly, stored at −20 to −80° C., from birth until discharge of the infants from the hospital. All blood samples of each baby were analyzed at the same time. Serum was diluted 1:50 and IGF-I was measured in duplicate by an IGFBP-blocked RIA, without extraction and in the presence of ~250-fold excess of IGF-II (Mediagnost GmbH, Tübingen, Germany). See. Blum W F, Breier B H. Radioimmunoassays for IGFs and IGFBPs. Growth Regulation 1994; 4:11–9. The intra-assay coefficient of variation (CV) at 10.2 µg/L and 34.5 µg/L was 15.7% and 9.6%, respectively. The interassay CV at 10.2 µg/L and 34.5 µg/L was 23.9% and 12.1%, respectively.

IGFBP-3 Analyses

The native concentrations of serum IGFBP-3 were diluted 1:300 and measured in duplicate, and determined using a RIA See. Blum W F, Breier B H. Radioimmunoassays for IGFs and IGFBPs. Growth Regulation 1994; 4:11–9. The intra-assay and interassay CV at 1773 ng/ml was 6.1% and 10.6%, respectively.

Morbidity Evaluation

ROP was classified according to the International Classification (Anonymous. An international classification of retinopathy of prematurity. Prepared by an international committee. British Journal of Ophthalmology 1984; 68:690–7) and subdivided into Stage 1(demarcation line), Stage 2 (ridge), Stage 3 (ridge with extraretinal fibrovascular proliferations), stage 4 (subtotal retinal detachment) and Stage 5 (total retinal detachment). The presence of dilatation of the posterior retinal vessels was referred to as "plus" disease. For the purpose of this study, ROP was defined as the presence of any stage higher than Stage 1 of the disease.

The severity of ROP was classified according to its most advanced stage. The infants were examined according to a routine protocol, which consisted of dilated eye fundus examinations from the chronological age of 5 to 6 weeks until the eyes were fully vascularized, if no ROP or Stage 1 ROP was found. If ROP Stage 2 or more was diagnosed, examinations were performed once or twice a week, depending on the severity of the disease, until the condition was considered stable with or without treatment. The infants' eyes were examined by indirect ophthalmoscopy after pupillary dilatation with 1% cyclogyl. Care was taken to minimize pain and stress during the examinations.

Other Morbidity Evaluation

The diagnosis bronchopulmonary dysplasia (BPD) was based on the typical appearance of BPD on serial chest x-rays and the need for oxygen supplementation at gestational week 36. See, Shennan A T, Dunn M S, Ohlsson A, Lennox K, Hoskins E M. Abnormal pulmonary outcomes in premature infants: prediction from oxygen requirement in the neonatal period. Pediatrics 1988; 82:527–32. The hospital file of each child was also reviewed for intracranial hemorrhage (IVH) (grade 2–4; diagnosed by perinatal cerebral ultrasonography (Burstein J, Papile L A, Burstein R. Intraventricular hemorrhage and hydrocephalus in premature newborns: a prospective study with CT. AJR. American Journal of Roentgenology 1979; 132:631–5)) and necrotizing enterocolitis (NEC) with gut perforation leading to surgery.

Statistical Analysis

In comparison of children with ROP Stage 0–1 and children with ROP Stage 2–3, the length of time from birth to reach IGF-I>30 µg/L and the mean level of available measurements of IGF-I at post-menstrual weeks 31–35 were analyzed with the Wilcoxon-Mann-Whitney U-test. A multiple logistic regression analysis was performed for ROP [8]. The potential explanatory variables in the model were post-menstrual or gestational age (GA), birth weight (BW) and the individual mean level of IGF-I during post-menstrual weeks 31–35. The model used was logit (ROP stage>1=1, else ROP=0)=$\alpha + \beta_1 \times GA$ (weeks)+$\beta_2 \times$Mean IGF-I week 31–35 (µg/L). Individual longitudinal serum IGF-I levels were used in the evaluation of the IGF-I pattern.

The postnatal morbidity was dichotomized as no morbidity (ROP Stage 0–1, no BPD, IVH Stage 0–1 and no NEC) or postnatal morbidity (ROP Stage 2–4, BPD, IVH Stage 2–4 or NEC). P-values less than 0.05 were considered significant.

Demographics of Participating Infants

The baseline characteristics of the infants with ROP (n=17) compared to those with no ROP (n=31) demonstrated that the children with ROP had lower gestational age and weight at birth, (Table 1).

IGF-I and ROP and Other Perinatal Morbidity

Figure 3:
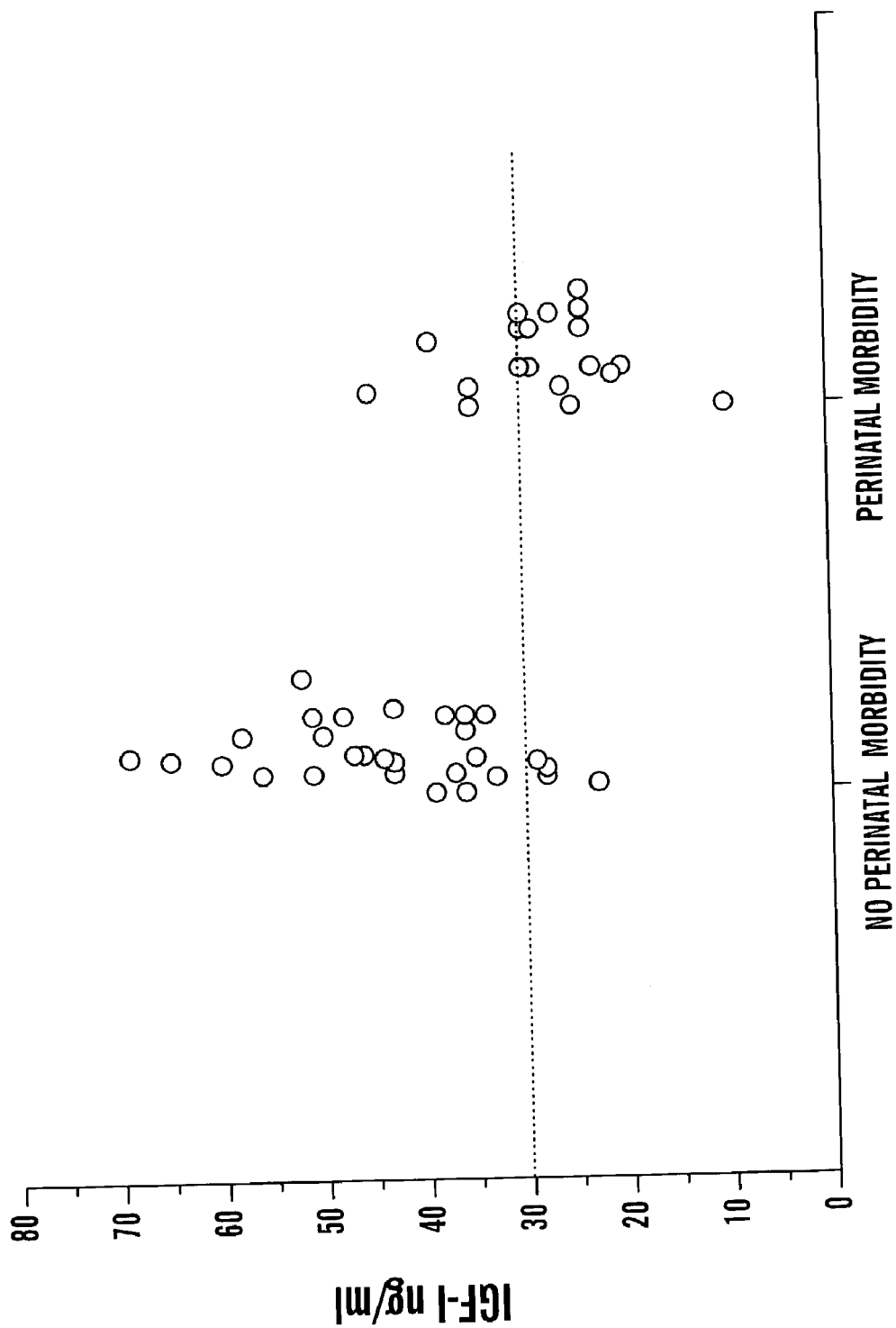
FIG. 3 shows serum IGF-I levels at 33 weeks of gestation in 29 children without perinatal morbidity and in 19 children with perinatal morbidity. The horizontal line indicates an IGF-I concentration of 30 µg/L. 25 of 29 children without postnatal morbidity but only 4 of 19 children with perinatal morbidity had values above 30 µg/L.

Nineteen of the 48 infants had postnatal morbidity (ROP, IVH, BPD or NEC) associated with preterm birth. Seventeen of the 19 infants with morbidity developed ROP, and 13 of the 17 with ROP had other morbidities in addition. In total 11 had BPD, 4 had NEC leading to surgery and 4 had IVH. Only 2 children had postnatal morbidity (IVH) without also having ROP (Table 2). A different longitudinal IGF-I pattern was found in the preterm infants with no or minimal ROP as compared to the group with ROP (FIG. 2). Preterm children with ROP Stage 0–1 (n=31) had a peak level of IGF-I at a gestational age of 31–35 weeks while preterm children with ROP Stage 2–3 (n=17) had a slow rise of IGF-I level without a peak (FIG. 2). The median duration of time from birth to IGF-I reaching 30 µg/L was 16 days (range 0–53 days) in infants with ROP Stage 0–1 (n=31), compared to 59 days (range 1–100 days) for those that developed ROP Stage 2–3 (n=17), (P<0.0001), FIG. 2. The median level of IGF-I at 31–35 weeks of gestation was 26 µg/L (range, 17–49 µg/L) for infants with ROP or other postnatal morbidity (n=19), compared to 38 µg/L (range 20–59 µg/L) in the group without postnatal morbidity (n=29), P<0.0001. At 33 gestational weeks, 4 of the 19 children with ROP or other postnatal morbidity had IGF-I values above 30 µg/L, while 15 children had IGF-I values $\leq$30 µg/L. Among the 29 children without postnatal morbidity, 25 children had IGF-I values above 30 µg/L while 4 children had values below 30 µg/L, FIG. 3. Thus, preterm children with IGF-I$\leq$30 µg/L at 33 weeks of gestation had a relative risk of 5.7 (95% confidence interval 2.2–14.6) to develop ROP or other postnatal morbidity. Among the 6 twin pairs in the study, the twin with more morbidity had the lowest IGF-I values (data not shown).

Mean IGF-I Compared with Post-Menstrual Age and Birth Weight

Figure 4:
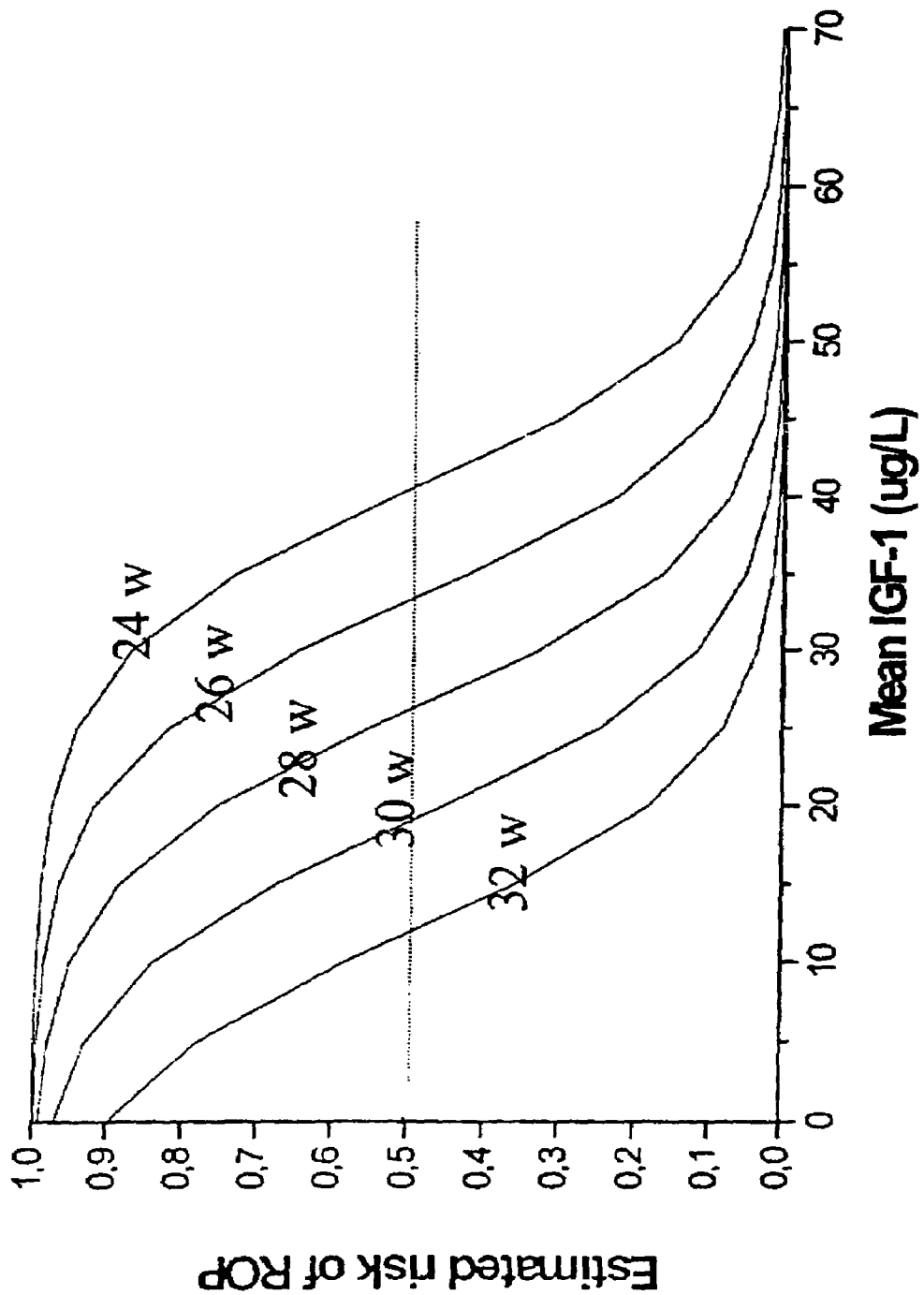
FIG. 4 shows relative impact of serum levels of IGF-I and post-menstrual GA on the risk for retinopathy of prematurity as estimated by multiple logistic regression analysis. Post-menstrual age at birth (24–32 weeks) indicated in the graph. The regression analysis shows that if post-menstrual age is 24 weeks at birth a mean IGF-I level at 31–35 weeks of 40 µg/L carries a risk of developing ROP of 50% (dashed line). However, if post-menstrual age is 32 weeks at birth, an IGF-I level of 12 µg/L carries a risk of developing ROP of 50%.

The results of the multiple regression analysis, taking IGF-I and post-menstrual GA into account, was logit (ROP Stage 2–3)=23—0.18 (mean IGF-I week 31–35/µg/L)—0.65 (GA/weeks). The relative risk of ROP associated with a 5 µg/L increase of mean IGF-I during post-menstrual weeks 31–35 was $e^{-0.9}$=0.41 when adjusting for post-menstrual age. Thus, an increase of 5 µg/L in mean IGF-I during post-menstrual weeks 31–35 decreased the risk of having ROP stage 2–3 by 59%, while an increase of 1 gestational week decreased the risk by 48% (FIG. 4). The results of the multiple regression analysis, taking IGF-I and BW into account, was logit (ROP Stage 2–3)=10—0.16 (mean IGF-I week 31–35/µg/L)–0.62 (BW/100 grams).

EXAMPLE 2

Measurement of Vessel Growth in IGF-1 Knockout Mice

These studies adhered to the ARVO Statement for the Use of Animals in Ophthalmic and Vision Research. IGF-I null mice (IGF-I$^{-/-}$) were generated through inbreeding mice carrying heterozygous IGF-I-flox$^{+/-}$ (L/−) on a mixed C57/129sv background. See, Liu, J. L. & LeRoith, D. (1999) *Endocrinology* 140, 5178–84. Born as dwarfs with severe developmental deficiency, only 40% of the few born survived postnatal life. Their littermates, L/L or L/− were virtually identical and normal. Genotyping using PCR and Southern blot analysis on tail DNA samples were performed as previously reported. See, Liu, J. L., Grinberg, A., Westphal, H., Sauer, B., Accili, D., Karas, M. & LeRoith, D. (1998) *Mol Endocrinol* 12, 1452–62. At post-natal day 5, 5 IGFI$^{-/-}$ and 6 IGF1$^{+/+}$ sibling mice were sacrificed and eyes were isolated, then fresh frozen in OCT and serially sectioned (8 µm). Thirty sections were made through the pupil and optic nerve and blood vessels stained with fluorescein-ated Griffonia Bandereiraea Simplicifolia Isolectin B4 (Vector Laboratories, Burlingame, Calif.). The length of vascularized retina was measured from the optic nerve along the surface of the ganglion layer to the edge of the vascular front, and represented as a percentage of the total length of the retina, from the optic nerve to the ora serrata.

Retinal Flat Mount

Eyes from 5 IGF-1$^{-/-}$ and 5 IGF-1$^{+/+}$ littermate control mice were enucleated at P5 following intracardiac perfusion with fluorescein-dextran in 4% paraformaldehyde. See, D'Amato, R., Wesolowski, E. & Smith, L. E. (1993) *Microvasc Res* 46, 135–42. Retinas were isolated, flat-mounted with glycerol-gelatin and photographed with a fluorescence microscope. VEGF mRNA was visualized according to standard protocol. See, Pierce, E. A., Foley, E. D. & Smith, L. E. (1996) *Arch Ophthalmol* 14, 1219–28.

Laser Capture Microdissection

OCT embedded eyes from 5 IGF-1$^{-/-}$ mice and 6 IGF-1$^{+/+}$ littermate controls were sectioned at 8 µm in a cryostat, mounted on uncoated glass slides and immediately stored at −80° C. Slides containing frozen sections were immediately fixed in 70% ethanol for 30 sec, stained with hematoxylin (Meyers) and eosin (H/E), followed by 5 second dehydration steps in 70%, 95% and 100% ethanol and a final 10 minute dehydration step in xylene. Once air-dried, the anterior avascular third of retinal sections were microdissected, without RPE contamination, with a PixCell II LCM system. (Arcturus Engineering, Mountain View, Calif.). Each population was estimated to be greater than 95% 'homogeneous' as determined by microscopic visualization of the captured cells. Material from 40 sections from >4 mice was combined, RNA isolated, converted to cDNA as described, and specific cDNA was quantified using qRT-PCR.

RNA/cDNA Isolation

Total RNA was isolated from pooled microdissected retina from IGF-1$^{-/-}$ and control IGF-1$^{+/+}$ mice. See, Chirgwin, J. M., Przybyla, A. E., MacDonald, R. J. & Rutter, W. J. (1979) *Biochemistry* 18, 5294–9. All cDNA samples were aliquoted and stored at −80° C. The VEGF mRNA compared to cyclophilin was measured for IGF-1$^{-/-}$ and control IGF-1$^{+/+}$ retina.

Analysis of VEGF Expression

PCR primers targeting VEGF and two unchanging control genes (cyclophilin and 18S) were designed using Primer Express software (Perkin Elmer, Norwalk, Conn.) and synthesized (Oligo Therapeutics, Wilsonville, Oreg.). Amplicons generated during the PCR reaction were gel purified and sequenced to confirm the selection of the desired sequence. Quantitative analysis of gene expression were generated using an ABI Prism 7700 Sequence Detection System (TaqMan®) and the SYBR Green master mix kit (Perkin Elmer, Norwalk, Conn.). VEGF: Forward 5'-GGAGATCCTTCGAGGAGCACTT-3' (SEQ ID NO:1), Reverse 5'-GGCGATTTAGCAGCAGATATAAGAA-3' (SEQ ID NO:2); Cyclophilin: Forward 5'-CAGACGC-CACTGTCGCTTT-3' (SEQ ID NO:3), Reverse 5'-TGTCTTTGGAACTTTGTCTGCAA-3' (SEQ ID NO:4); 18S ribosomal RNA: Forward 5'-CGGCTACCA-CATCCAAGGAA-3' (SEQ ID NO:5), Reverse 5'-GCTG-GAATTACCGCGGCT-3' (SEQ ID NO:6).

Clinical Studies

On an IRB-approved protocol, all children with a gestational age less than 32 weeks at birth and without any obvious abnormalities born at The Queen Silvia Children's Hospital, Göteborg between Dec. 15, 1999 and Mar. 15, 2000 were invited to participate in the present study. With written consent, 0.5 ml blood was collected weekly from birth to hospital discharge. Serum IGF-I was measured in duplicate by an IGFBP-blocked RIA, without extraction and in the presence of ~250-fold excess IGF-II (Blum, W. F. & Breier, B. H. (1994) *Growth Regulation* 4, 11–9) (Mediagnost GmbH, Tübingen, Germany). The intra-assay CV were 8.1, 4.4, and 4.5% at concentrations of 55, 219 and 479 µg/L, respectively, and the interassay CV were 10.4, 7.7, 5.3% at concentrations 55, 219, 479 µg/L, respectively.

ROP Examinations

Dilated retinal examinations with indirect ophthalmoscopy were performed weekly or biweekly from the age of 5 to 6 weeks until the retina was fully vascularized or the condition considered stable. Children with plus disease and/or Stage 3 ROP had more frequent examinations. ROP changes were classified according to the International Classification of ROP.

Retinal Endothelial Cells and Analyses of AKT Phosphorylation

Experiments with bovine retinal endothelial cells (VEC Technologies, Rensselaer, N.Y.) were performed four times with similar results. Moreover, similar results were obtained with separate bovine retinal endothelial cell populations isolated as described previously. See, Smith, L. E., Shen, W., Perruzzi, C., Soker, S., Kinose, F., Xu, X., Robinson, G., Driver, S., Bischoff, J., Zhang, B., Schaeffer, J. M. & Senger, D. R. (1999) *Nature Medicine* 5, 1390–5. For analyses of AKT phosphorylation, cells were grown in complete culture medium (MCDB-131 Complete) (VEC Technologies, Rensselaer, N.Y.) to confluence in 24 well plates coated with bovine collagen type 1 (50 µg/ml Vitrogen, (Cohesion Co., Palo Alto, Calif.). At confluence, cells were shifted for several days to endothelial basal medium (EBM) (Clonetics, San Diego, Calif.) containing 2% fetal bovine serum to reduce baseline phosphorylation of AKT. On the day of assay, cells were shifted to serum-free EBM for four hours to reduce baseline further and then stimulated with VEGF, IGF-1, or both (R&D Systems, Minneapolis, Minn.) as indicated. Cells were lysed in electrophoresis sample buffer and subjected to electrophoresis in 10% polyacrylamide gels followed by electro-blotting as described (Id.). Blots were stained with phospho-AKT antibody (Ser-473, Pharmingen, San Diego, Calif.), secondary antibody, and chemiluminescent substrate also as described (Id.). To visualize total AKT, replicate blots were prepared and stained with an antibody, which binds both phosphorylated and non-phosphorylated AKT (H-136, Santa Cruz Biotechnology, San Diego, Calif.).

IGF-I is Critical for Normal Retinal Vascular Growth

To test whether IGF-1 is critical for normal retinal vascular development and therefore critical to the development of ROP (Flynn, J. T., O'Grady, G. E., Herrera, J., Kushner, B. J., Cantolino, S. & Milam, W. (1977) *Arch Ophthalmol* 95, 217–23; and Penn, J. S., Tolman, B. L. & Henry, M. M. (1994) *Invest Ophthalmol Vis Sci* 35, 3429–35), we examined retinal vessels in IGF-I$^{-/-}$ mice (which lack both circulating and local IGF-1) and their normal littermate controls (IGF-I$^{+/+}$). The systemic level of IGF-1 (versus local production) contributes most significantly to retinopathy. See, Spranger, J., Buhnen, J., Jansen, V., Krieg, M., Meyer-Schwickerath, R., Blum, W. F., Schatz, H. & Pfeiffer, A. F. H. (2000) *Hormone & Metabolic Research* 32, 196–200.

Figure 5B:
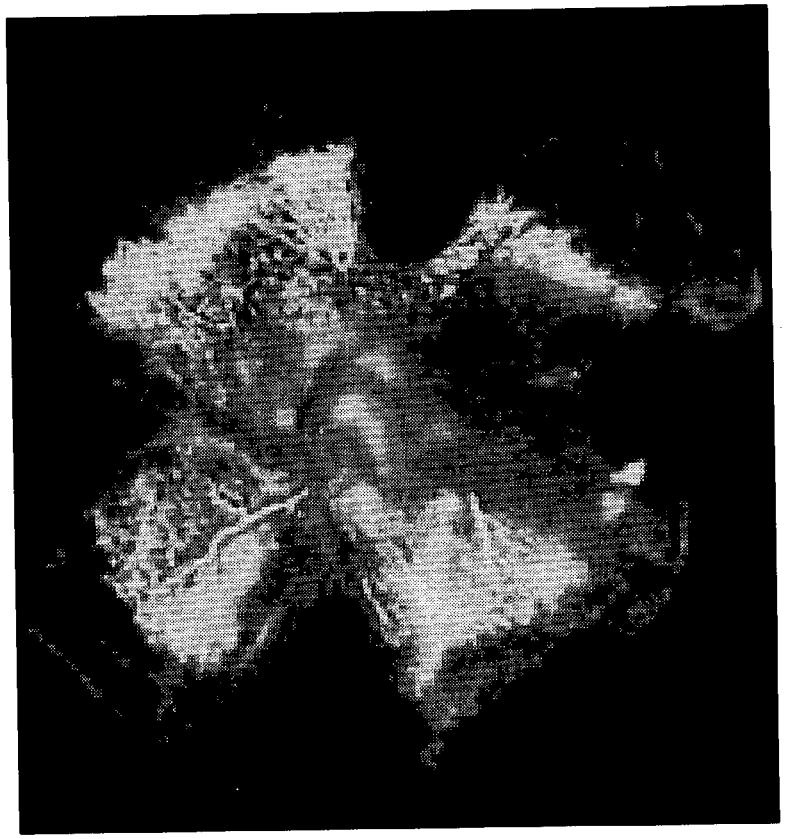
FIGS. 5A–B illustrate effect of IGF-1 inhibition on vascular growth. Flat-mounted whole retina shows that in IGF-$1^{-/-}$ mice (FIG. 5A) there is less progression of vascular development (bright area) compared to IGF-$1^{+/+}$ littermate controls (FIG. 5B).
Figure 5A:
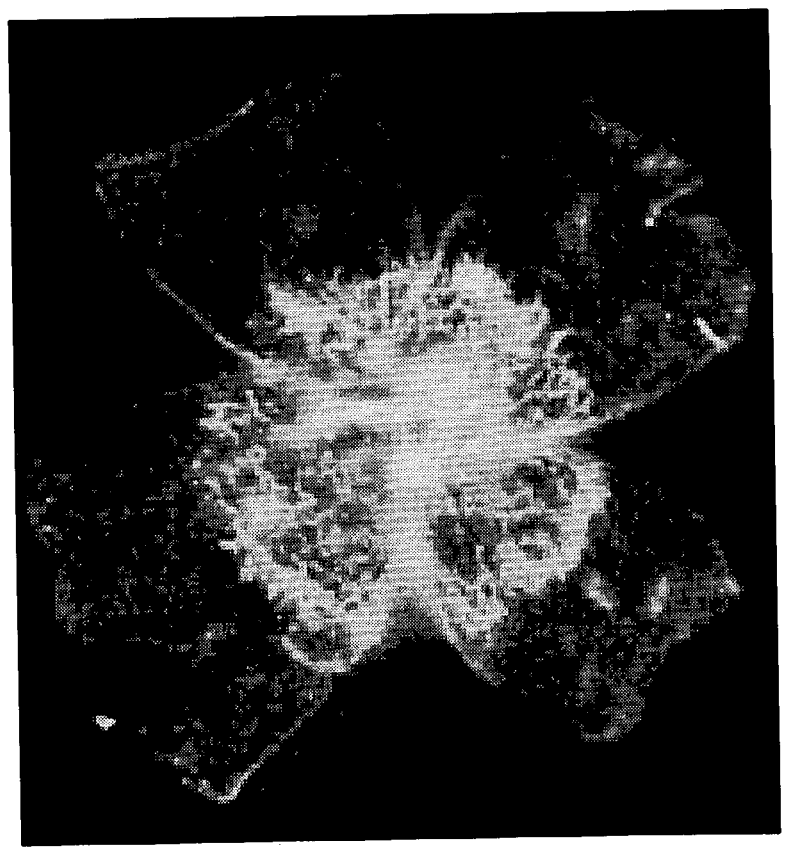

Mice were perfused with FITC dextran at postnatal day 5 (P5), eyes enucleated and retinas examined in cross section and flat mount. There was significantly retarded vascular growth in the eyes of the IGF-1$^{-/-}$ mice (FIG. 5A) compared to IGF-1$^{+/+}$ controls with normal IGF-1 levels (FIG. 5B). At P5 the percent distance of the vessels from optic nerve to periphery was 58±4.8% for IGF-1$^{-/-}$ retinas versus 70.3±5.8% for IGF-1$^{+/+}$ controls (P<0.001) indicating that IGF-1 is critical for normal vascular development and that low IGF-1 in the neonatal period could cause retardation of vascular growth.

Figure 6A:
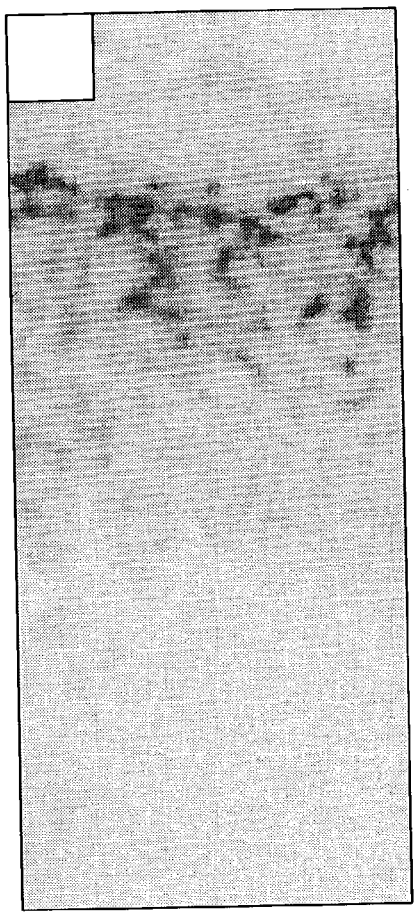
FIGS. 6A–B show a laser microdissection of retina anterior to growing vessels.
Figure 6B:

VEGF is an important factor in normal vessel development and is found anterior to the growing vascular front. See, Pierce, E. A., Foley, E. D. & Smith, L. E. (1996) Arch Ophthalmol 114, 1219–28; Stone, J., Itin, A., Alon, T., Pe'er, J., Gnessin, H., Chan-Ling, T. & Keshet, E. (1995) J Neurosci 15, 4738–47; and Alon, T., Hemo, I., Itin, A., Pe'er, J., Stone, J. & Keshet, E. (1995) Nature Medicine 1, 1024–8. Vessels grow towards the moving wave of VEGF, which is induced as unvascularized retina matures anteriorly (physiological hypoxia) and is then suppressed posteriorly as vessels supply oxygen (FIG. 6A). Inhibition of VEGF can cause retardation of vascular growth. See, Aiello, L. P., Pierce, E. A., Foley, E. D., Takagi, H., Chen, H., Riddle, L., Ferrara, N., King, G. L. & Smith, L. E. (1995) Proc Natl Acad Sci USA 92, 10457–61; Robinson, G. S., Pierce, E. A., Rook, S. L., Foley, E., Webb, R. & Smith, L. E. (1996) Proc Natl Acad Sci USA 93, 4851–6; and Ozaki, H., Seo, M. S., Ozaki, K., Yamada, H., Yamada, E., Okamoto, N., Hofmann, F., Wood, J. M. & Campochiaro, P. A. (2000) American Journal of Pathology 156, 697–707. To test if the effect of low IGF-1 on inhibition of vascular growth was due to absence of VEGF, we laser microdissected the area of retina anterior to blood vessels in P5 IGF-1$^{-/-}$ and control IGF-1$^{+/+}$ retinal cross sections to detect VEGF mRNA using qRT-PCR (FIG. 6B). Anterior to the vessels in both IGF-1$^{-/-}$ and IGF-1$^{+/+}$ control retinas, VEGF mRNA was present in comparable amounts relative to cyclophilin control as measured by qRT PCR. Thus low IGF-1 does not inhibit vascular growth through suppression of VEGF. See, Smith, L. E., Shen, W., Perruzzi, C., Soker, S., Kinose, F., Xu, X., Robinson, G., Driver, S., Bischoff, J., Zhang, B., Schaeffer, J. M. & Senger, D. R. (1999) Nature Medicine 5, 1390–5 and Smith, L. E., Kopchick, J. J., Chen, W., Knapp, J., Kinose, F., Daley, D., Foley, E., Smith, R. G. & Schaeffer, J. M. (1997) Science 276, 1706–9. IGF-I control is either downstream of VEGF or permissive to its action in vascular development. This data also supports the hypothesis that VEGF, in the absence of IGF-1, cannot stimulate normal retinal vascular development.

To test the hypothesis that a prolonged period of low IGF-1 levels after birth was associated with lack of vascular growth followed by ROP in premature infants, we prospectively measured IGF-1 plasma levels weekly after birth and coordinately examined retinas in all premature infants born at gestational ages 26 to 30 weeks at high risk for ROP (n=31). ROP stages 0–4 were defined according to the International Classification (Flynn, J. T. (1985) *Ophthalmology* 92, 987–94) and for our studies ROP stages 2–5 was defined as ROP and ROP stages 0–1 as no ROP.

We first confirmed that lack of vascular growth is associated with proliferative ROP. See, Flynn, J. T., O'Grady, G. E., Herrera, J., Kushner, B. J., Cantolino, S. & Milam, W. (1977) *Arch Ophthalmol* 95, 217–23. The normal immature retina has a gradual transition from translucent vascularized retina into gray non-vascularized retina without a distinct border between the two. In ROP, a sharp observable stationary border consisting of a line or ridge between vascularized and non-vascularized retina becomes apparent. In all patients with ROP (n=10) there was a demarcation line anterior to which no vessels were seen. In all infants without ROP (n=19) there was no ridge and no demarcation line indicating more normal growth of the vascular front (data not shown).

Figure 7:
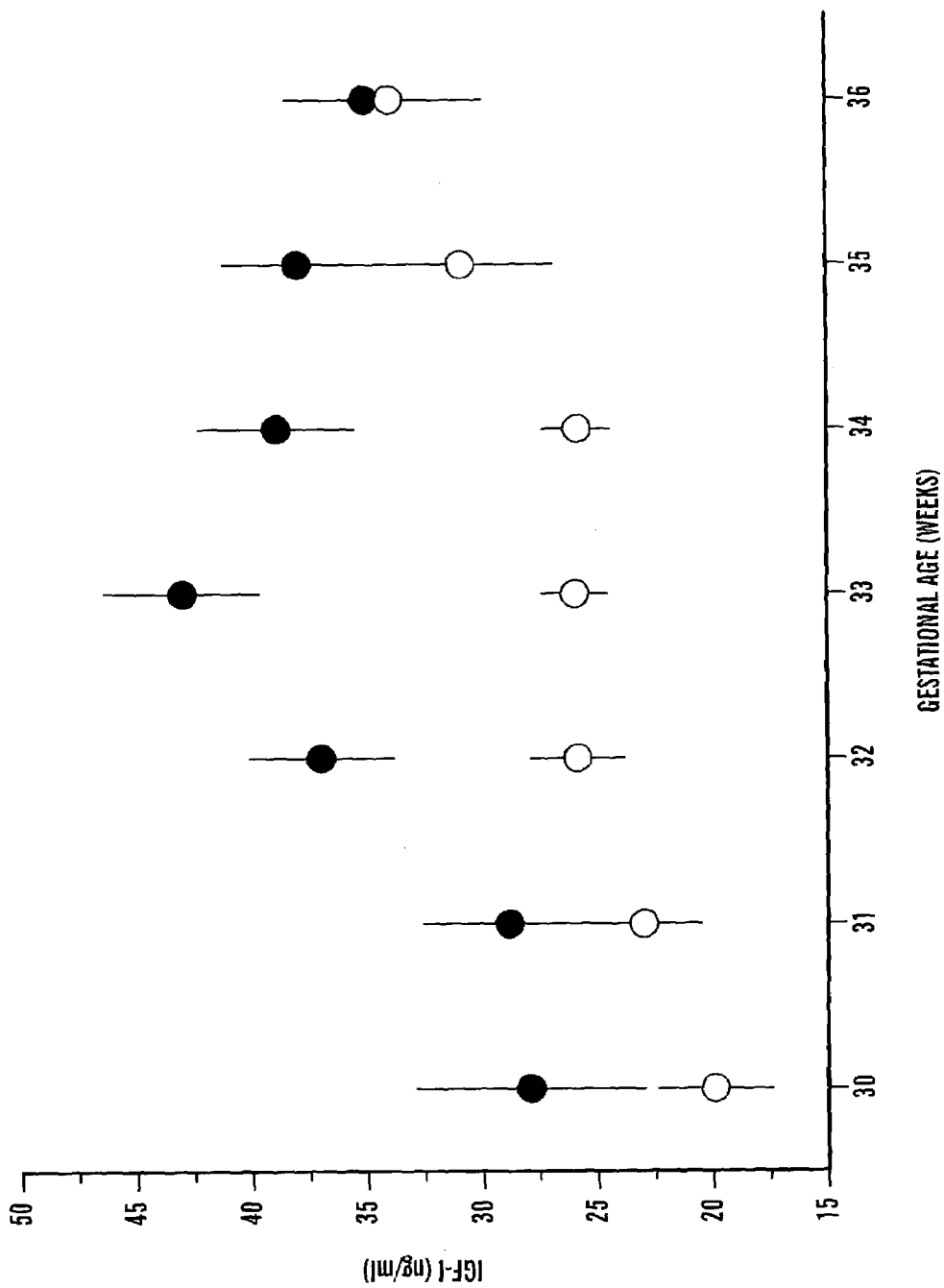
FIG. 7 illustrates mean serum IGF-I at matched gestational ages in infants with and without ROP. The mean IGF-1 level for infants with ROP (white circles) and without ROP (dark circles) is shown versus gestational age. Error bars indicate standard error of the mean.

The mean duration of time from birth to IGF-1 reaching 30 ng/ml was 19 days (range 1–79) in infants who developed no ROP (n=19) compared to 58 days (range 29–120) for those that developed ROP (n=10), (P≦0.0001) confirming the hypothesis that prolonged low levels of IGF-1 were associated with ROP. IGF-1 might be lower in utero in younger fetuses and therefore related simply to gestational age. However, the mean IGF-1 level at the same gestational age was consistently lower in infants who developed ROP than those who did not develop ROP with a difference at 34 weeks of 25 ng/ml for ROP (range 21–35) versus 43 ng/ml for no ROP (range 11–58) (P≦0.002). Maximum IGF-I in the period gestational age 30–35 weeks was significantly lower among the children with ROP (38 ng/ml (range 28–54 ng/ml)) than the children without ROP (52 ng/ml (range 29–90 ng/ml)) P<0.04. In all infants who developed ROP, the onset of the proliferative phase of ROP did not occur before IGF-1 levels increased to >30 ng/ml. In summary, the development of ROP was strongly associated with a prolonged period of low IGF-1 (<30 ng/ml) followed by rise to "threshold" (>30 ng/ml) at .about.34–35 weeks gestation, the mean onset of proliferative ROP in our cohort. Infants with early higher IGF-1 levels had more normal vascular development and did not develop ROP (FIG. 7).

Late stage ROP is characterized by initial cessation of vascular growth followed by a sudden proliferation of neovascularization at ~34 weeks post conceptual age, whatever the chronological age of the infant. We postulated that low IGF-1 prevented maximum VEGF-induced endothelial cell function because there was a supporting effect of IGF-1 on VEGF-regulated retinal vascular endothelial cell survival and proliferation. We have previously shown that IGF-1 is required for maximum VEGF stimulation of the MAPK pathway, important to cell proliferation. See, Smith, L. E., Shen, W., Perruzzi, C., Soker, S., Kinose, F., Xu, X., Robinson, G., Driver, S., Bischoff, J., Zhang, B., Schaeffer, J. M. & Senger, D. R. (1999) *Nature Medicine* 5, 1390–5.

Figure 8:
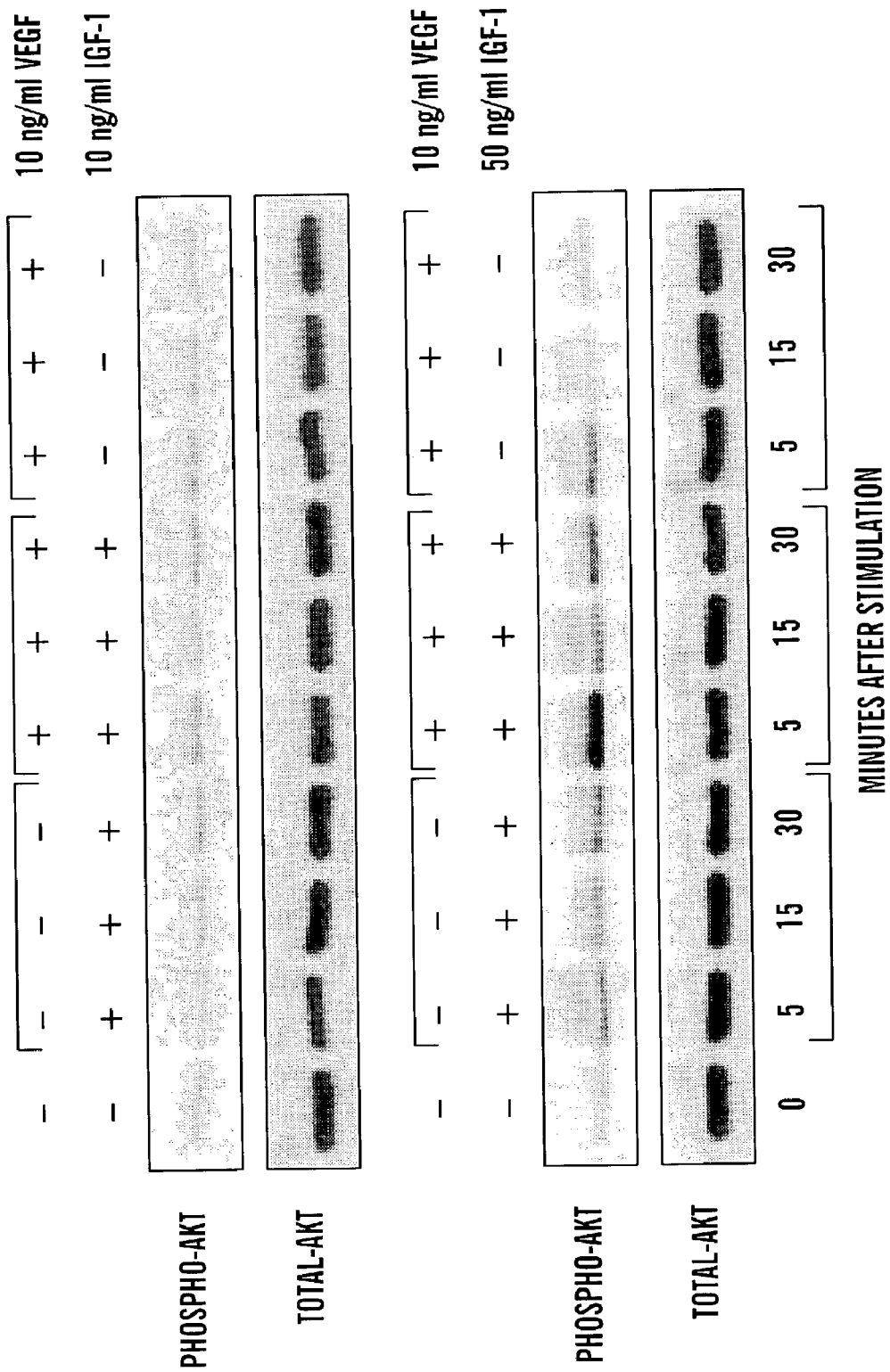
FIG. 8 shows replicate blots prepared from total cell lysates and stained either with phospho-AKT (Ser 473) antibody or antibody which recognizes AKT irrespective of phosphorylation status (total-AKT). Following serum starvation to reduce baseline AKT phosphorylation, cells were stimulated with VEGF, IGF-1, or both for times indicated.

Cell survival, which is also critical to both phases of ROP, is associated with activation of the AKT pathway, which can be accomplished in endothelial cells by stimulation with sufficient concentrations of VEGF (Carmeliet, P., Lampugnani, M. G., Moons, L., Breviario, F., Compernolle, V., Bono, F., Balconi, G., Spagnuolo, R., Oostuyse, B., Dewerchin, M., Zanetti, A., Angellilo, A., Mattot, V., Nuyens, D., Lutgens, E., Clotman, F., de Ruiter, M. C., Gittenberger-de Groot, A., Poelmann, R., Lupu, F., Herbert, J. M., Collen, D. & Dejana, E. (1999) Cell 98, 147–57; Fujio, Y. & Walsh, K. (1999) Journal of Biological Chemistry 274, 16349–54; and Gerber, H. P., McMurtrey, A., Kowalski, J., Yan, M., Keyt, B. A., Dixit, V. & Ferrara, N. (1998) Journal of Biological Chemistry 273, 30336–43.) or IGF-1 (Michell, B. J., Griffiths, J. E., Mitchelhill, K. I., Rodriguez-Crespo, I., Tiganis, T., Bozinovski, S., de Montellano, P. R., Kemp, B. E. & Pearson, R. B. (1999) Current Biology 9, 845–8.). However, the possibility that these two cytokines exert complementary effects towards AKT activation had not been explored. Therefore, we tested the effects of IGF-1 on VEGF activation of AKT in retinal endothelial cells. We found that VEGF (10 ng/ml) and IGF-1 (50 ng/ml) individually stimulated modest increases in AKT phosphorylation (2.5-fold), but that both together stimulated a 5-fold increase (FIG. 8). However, the complementary action of VEGF and IGF-1 towards stimulation of AKT phosphorylation was not observed when IGF-1 was reduced to 10 ng/ml. Thus, these data indicate that 50 ng/ml IGF-1, which approximates a more normal physiological circulating concentration in newborns, acts together with VEGF to activate AKT (as indicated by phosphorylation of serine 473), and therefore supports endothelial cell survival in retina. By contrast, when IGF-1 is reduced to 10 ng/ml, comparable to the serum level present in premature infants likely to develop ROP, no such complementarity with VEGF is observed. Consequently, in such patients, lower than normal levels of IGF-1 likely translate into reduced AKT activation and reduced endothelial cell survival, despite the presence of a constant level of VEGF.

Discussion

These studies demonstrate that IGF-1 is necessary for vascular growth and rationalize the disease process of ROP, which begins with cessation of the growth of retinal vessels after premature birth. A key difference between vascular growth in utero and after birth is that IGF-1 falls in premature infants after birth. See, Lineham, J. D., Smith, R. M., Dahlenburg, G. W., King, R. A., Haslam, R. R., Stuart, M. C. & Faull, L. (1986) *Early Hum Dev* 13, 37–46. Our findings suggest that if IGF-1 increases quickly in premature infants after delivery, allowing normal vascular development, ROP does not occur.

Figures 9A, 9B, 9C, 9D:
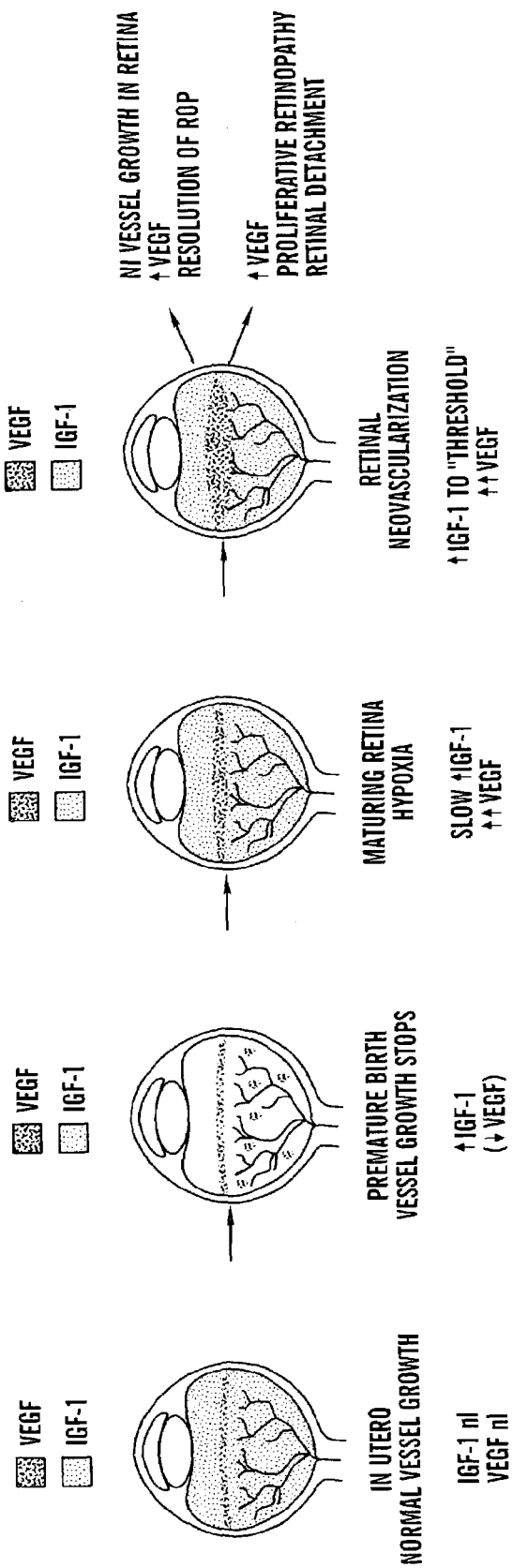
FIGS. 9A–D are a schematic representation of IGF-1/VEGF control of blood vessel development in ROP.

VEGF has been shown to play a significant role in the development of blood vessels but is insufficient in the presence of low IGF-1 levels to allow blood vessel growth. See, Smith, L. B., Shen, W., Perrurzi, C., Soker, S., Kinose, F., Xu, X., Robinson, G., Driver, S., Bischoff J., Zhang, B., Schaeffer, J. M. & Senger, D. R. (1999) Nature Medicine 5, 1390–5; and Smith, L. E., Kopehick, J. J., Chen, W., Knapp, J., Kinose, F., Daley, D., Foley, E., Smith, R. G. & Schaeffer, J. M. (1997) Science 276, 1706–9. VEGF is produced in the increasingly hypoxic avascular retina as metabolic demands increase with development and VEGF levels rise in the vitreous. See, Aiello, L. P., Avery, R. L., Arrigg, P. G., Keyt, B. A., Jampel, H. D., Shah, S. T., Pasquale, L. R., Thieme, H., Iwamoto, M. A., Park, J. E. & et al. (1994) N Engl J Med 331, 1480–7; and Miller, J. W., Adamis, A. P. & Aiello, L. P. (1997) Diabetes Metab Rev 13, 37–50. When IGF-1 rises more quickly after birth as occurs in the non-ROP infants, VEGF does not accumulate since vascular growth can occur which provides oxygen to the maturing retina and controls VEGF production. See, Pierce, E. A., Foley, E. D. & Smith, L. E. (1996) Arch Ophthalmol 114, 1219–28; and Stone, J., Itin, A., Alon, T., Pe'er, J., Gnessin, H., Chan-Ling, T. & Keshet, E. (1995) J Neurosci 15, 4738–47. When IGF-1 is low for an extended period, vessels cease to grow, maturing avascular retina becomes hypoxic and VEGF accumulates in the vitreous. As IGF-1 rises to a threshold level with high levels of VEGF present, a rapid growth of new blood vessels (retinal neovascularization) is triggered (FIG. 9). This rapid vascular growth is likely based on increased survival and proliferation of vascular endothelial cells since IGF-1 and VEGF are complementary for endothelial cell function through the MAPK and AKT signal transduction pathways. In particular, our data indicate that IGF-1 (and perhaps other cytokines) is necessary at minimal levels to promote maximum function of VEGF.

This work has direct clinical implications for diagnosis and treatment of ROP. These findings suggest that IGF-1 levels can be used to predict which babies will develop ROP. The differences in pattern of IGF-1 levels between patients that do and do not develop ROP suggest that increasing serum IGF-1 early after birth may prevent this disease. After premature birth potential sources of IGF-1 are lost, including ingestion of amniotic fluid, which contains high levels of IGF-1. IGF-1 may be increased to the levels found in infants without ROP through increased caloric intake (17), oral ingestion of IGF-1 to mimic ingestion of amniotic fluid (34), or an intravenous supply to raise IGF-1 to a more normal level. Since ROP is correlated with other developmental problems, increasing IGF-1 levels to the level of infants without ROP may also improve neurological development (Johnston, B. M., Mallard, E. C., Williams, C. E. & Gluckman, P. D. (1996) *J Clin Invest* 97, 300–8) and somatic growth (Kimble, R. M., Breier, B. H., Gluckman, P. D. & Harding, J. E. (1999) *Journal of Endocrinology* 162, 227–35).

Both IGF-1 and VEGF are also important in the second or neovascular phase of ROP. See, Anonymous. An international classification of retinopathy of prematurity. Prepared by an international committee. British Journal of Ophthalmology 1984; 68:690–7; Shennan A T, Dunn M S, Ohlsson A, Lennox K, Hoskins E M. Abnormal pulmonary outcomes in premature infants: prediction from oxygen requirement in the neonatal period. Pediatrics 1988; 82:527–32; Burstein J, Papile L A, Burstein R. Intraventricular hemorrhage and hydrocephalus in premature newborns: a prospective study with CT. AJR. American Journal of Roentgenology 1979; 132:631–5; Smith, L. E., Shen, W., Perruzzi, C., Soker, S., Kinose, F., Xu, X., Robinson, G., Driver, S., Bischoff, J., Zhang, B., Schaeffer, J. M. & Senger, D. R. (1999) *Nature Medicine* 5, 1390–5; and Smith, L. E., Kopchick, J. J., Chen, W., Knapp, J., Kinose, F., Daley, D., Foley, E., Smith, R. G. & Schaeffer, J. M. (1997) *Science* 276, 1706–9. IGF-1 is critical for retinal neovascularization. See, Smith, L. E., Shen, W., Perruzzi, C., Soker, S., Kinose, F., Xu, X., Robinson, G., Driver, S., Bischoff, J., Zhang, B., Schaeffer, J. M. & Senger, D. R. (1999) *Nature Medicine* 5, 1390–5. Thus although we would predict that early intervention to increase IGF-1 would allow normal vascular growth and prevent the development of the second potentially destructive phase of ROP, late intervention after accumulation of VEGF might trigger or exacerbate retinal neovascularization.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The references cited throughout the application are incorporated herein by reference.

TABLE I

BASE-LINE CHARACTERISTICS OF INFANTS WITH AVAILABLE OUTCOME DATA*

| CHARACTERISTICS | NON ROP (N = 31) | ROP (N = 17) |
| --- | --- | --- |
| Birth Weight (g) | | |
| 750 g | 2 | 7 |
| 750–999 g | 9 | 8 |
| >1000 g | 20 | 2 |
| Mean (g) | 1195.8 ± 353.6 | 780.6 ± 164.1 |
| Gestational age (wk) | | |
| <–27 wk | 10 | 13 |
| 28–31 wk | 21 | 4 |
| Mean (wk) | 28.2 ± 1.9 | 25.9 ± 1.6 |
| Males (% total) | 14(45%) | 6(55%) |
| Singletons (% of total) | 22(76%) | 12(71%) |

*Plus-Minus values are means ± SD. Because of rounding, percentages may not total 100.

TABLE II

INCIDENCE OF ROP AND OTHER PERINATAL MORBIDITY IN 48 CHILDREN BORN VERY PRETERM

| MORBIDITY | NUMBER OF INFANTS (% of total) |
|---|---|
| Any ROP | 17(35%) |
| ROP without other complications | 4(8%) |
| ROP, BPD & IVH | 2(4%) |
| ROP, BPD & NEC | 2(4%) |
| ROP & BPD | 7(15%) |
| ROP & NEC | 2(4%) |
| IVH | 2(4%) |
| Any Morbidity | 19(40%) |

*ROP; retinopathy of prematurity (stage 2–3), BPD; bronchopulmonary dysplasia, NEC; necrotizing enterocolitis, IVH; intraventricular hemorrhage (grade 2–3). Because of rounding, percentages may not total 100.

The invention claimed is:

1. A method for determining the risk of developing a complication of preterm birth in a patient born before 40 weeks of gestation or weighing 10% less than the average for the patient's gestational age comprising:
   (a) obtaining a blood sample from the patient after birth;
   (b) measuring postnatal serum levels of IGF-I and/or IGF binding protein in the blood sample, wherein the IGF binding protein is capable of binding IGF-I, to obtain an IGF-I or IGF binding protein level; and
   (c) comparing said postnatal IGF-I or IGF binding protein levels with an in utero baseline level of IGF-I or IGF binding protein based on gestational age matched mean levels in utero, wherein a postnatal IGF-I or IGF binding protein level below about the 90 percent confidence interval for the matched gestational age in utero level indicates the patient is at an increased risk of developing a complication of preterm birth, wherein the complication of preterm birth is selected from the group consisting of retinopathy of prematurity, developmental delay, mental retardation, bronchopulmonary dysplasia, necrotizing entercolitis, and intraventricular hemorrhage.

2. A method for determining the risk of developing a complication of preterm birth in a patient born before 40 weeks of gestation or weighing 10% less than the average for the patient's gestational age comprising:
   (a) obtaining a blood sample from the patient after birth;
   (b) measuring postnatal serum levels of IGF-I and/or IGF binding protein in the blood sample, wherein the IGF binding protein is capable of binding IGF-I, to obtain an IGF-I or IGF binding protein level; and
   (c) comparing said postnatal IGF-I or IGF binding protein levels with a baseline level of IGF-I or IGF binding protein based on gestational age matched mean levels of patients born before 40 weeks of gestation or weighing 10% less than the average for the patient's gestational age that do not develop complications of preterm birth, wherein a postnatal IGF-I or IGF binding protein level below the mean gestational age level of patients that do not develop complications of preterm birth indicates the patient is at an increased risk of developing a complication of preterm birth, wherein the complication of preterm birth is selected from the group consisting of retinopathy of prematurity, developmental delay, mental retardation, bronchopulmonary dysplasia, necrotizing entercolitis, and intraventricular hemorrhage.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
ggagatcctt cgaggagcac tt                                              22

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
ggcgatttag cagcagatat aagaa                                           25

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
cagacgccac tgtcgcttt                                                  19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
tgtctttgga actttgtctg caa                                             23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

```
<400> SEQUENCE: 5
cggctaccac atccaaggaa                                              20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
gctggaatta ccgcggct                                                18
```